(12) United States Patent
Katsumi et al.

(10) Patent No.: US 8,580,210 B2
(45) Date of Patent: Nov. 12, 2013

(54) SAMPLE ASPIRATING APPARATUS AND SAMPLE ANALYZER

(75) Inventors: Hironori Katsumi, Kobe (JP); Jun Inagaki, Himeji (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/210,982

(22) Filed: Aug. 16, 2011

(65) Prior Publication Data

US 2012/0045366 A1    Feb. 23, 2012

(30) Foreign Application Priority Data

Aug. 18, 2010  (JP) ................................. 2010-182735

(51) Int. Cl.
*B01L 3/02* (2006.01)
*G01N 1/10* (2006.01)

(52) U.S. Cl.
USPC ........... 422/512; 422/501; 422/509; 422/518; 422/521; 422/546; 422/63; 422/67; 73/864.74

(58) Field of Classification Search
USPC ................. 422/501, 509, 518, 519, 546, 570, 422/62–68.1, 500, 510–512, 520–521; 73/864.74, 427
See application file for complete search history.

(56) References Cited

U.S. PATENT DOCUMENTS

| 6,171,280 | B1 | 1/2001 | Imazu et al. | |
| 7,939,032 | B2 * | 5/2011 | Hanafusa et al. | 422/500 |
| 8,257,538 | B2 * | 9/2012 | Doi et al. | 156/241 |
| 2006/0216208 | A1 * | 9/2006 | Li et al. | 422/100 |
| 2006/0263250 | A1 * | 11/2006 | Blouin et al. | 422/63 |
| 2007/0104615 | A1 * | 5/2007 | Hanafusa et al. | 422/65 |
| 2010/0104478 | A1 * | 4/2010 | Kondou | 422/100 |
| 2012/0156098 | A1 * | 6/2012 | Sano et al. | 422/68.1 |

FOREIGN PATENT DOCUMENTS

JP    61-275660 A    12/1986

* cited by examiner

*Primary Examiner* — Brian R Gordon
(74) *Attorney, Agent, or Firm* — Sughrue Mion, PLLC

(57) ABSTRACT

A sample aspirating apparatus including a pipette which aspirates a sample, wherein the pipette is able to penetrate a cap of a capped container; a cap sensor which detects the cap of the capped container; a driving section which moves the pipette upward and downward; a crash sensor which detects a crash of the pipette with an obstacle; and a controller which controls the driving section to move the pipette, and stop the pipette when the crash sensor detects a crash by the pipette, wherein when aspirating a sample from a container after the cap sensor has detected a cap, the controller controls the driving section to move the pipette downward regardless of the detection by the crash sensor and thereby cause the pipette to penetrate the cap of the container. A sample analyzer which includes the above mentioned sample aspirating apparatus is also disclosed.

20 Claims, 18 Drawing Sheets

SAMPLE ASPIRATING APPARATUS AND SAMPLE ANALYZER

FIELD OF THE INVENTION

The present invention relates to a sample aspirating apparatus, and more specifically relates to a sample aspirating apparatus capable of aspirating a sample from a capped sample container and from an uncapped sample container. The present invention further relates to a sample analyzer with a sample aspirating device.

BACKGROUND

Conventional sample aspirating apparatuses are known which aspirate a sample from a container via a pipette inserted in the container. Among such sample aspirating apparatuses, there are known sample aspirating apparatuses which, when lowering the pipette toward the sample container, stop the lowering of the pipette when pipette crash is detected to prevent damage to the pipette via the crash of the pipette with an obstruction (for example, Japanese Laid-Open Patent Publication No. 61-275660).

Among the sample aspirating apparatuses capable of detecting crash of the pipette, a sample aspirating apparatus is known which is capable of aspirating a sample from a capped sample container (for example, U.S. Pat. No. 6,171,280).

U.S. Pat. No. 6,171,280 discloses a liquid aspirating apparatus incorporating a pipette having a sharp tip and capable of aspirating a liquid, two types of drive sources of relative strength to move the pipette upward and downward, and an external force detecting means which detects the action of an upward external force on the pipette. This apparatus stops the lowering of the pipette when the external force detecting means detects a collision of the pipette with an obstacle. This apparatus determines the container is an open container when the pipette is moved toward the container via a first drive source and no external force is detected by the external force detecting means, and determines the container is a sealed container sealed by a cap when an external force is detected by the external force detecting means. When the container is determined to be a sealed container, the pipette is pulled away from the cap of the container, and the pipette is then lowered by switching the drive source from the first drive source to a second drive source that is stronger than the first drive source, whereby the cap of the container is penetrated by the pipette.

When an external force is applied to the external force detecting means, an external force detecting means can not determine a detected external force is created by a collision of a pipette and a cap of container or by a collision of a pipette and another obstacle other than the cap. Therefore, it will be cause a trouble of control when penetrating the pipette to the cap of the container while functioning the external force detecting means.

In the sample aspirating apparatus disclosed in U.S. Pat. No. 6,171,280, when the pipette penetrates the cap of the container, the pipette is lowered after switching from the first drive source which imparts a drive force to the pipette through the external force detecting means to the second drive source which imparts a drive force directly to the pipette by bypassing the external force detecting means when the pipette is penetrating the cap of the container. However, this configuration requires an extremely complex structure.

SUMMARY OF THE INVENTION

A first aspect of the present invention is a sample aspirating apparatus capable of aspirating a sample from both a capped container with a cap and an uncapped container, the sample aspirating apparatus comprising: a pipette which aspirates a sample, wherein the pipette is able to penetrate a cap of a capped container; a cap sensor which detects the cap of the capped container; a driving section which moves the pipette upward and downward; a crash sensor which detects a crash of the pipette with an obstacle; and a controller which controls the driving section to move the pipette, and stop the pipette when the crash sensor detects a crash by the pipette, wherein when aspirating a sample in a container with a cap which is detected by the cap sensor, the controller controls the driving section to move the pipette downward regardless of the detection by the crash sensor and thereby cause the pipette to penetrate the cap.

A second aspect of the present invention is a sample analyzer which measures and analyzes a measurement sample prepared by adding a reagent to the sample, the sample analyzer comprising: the sample aspirating apparatus of claim 1; a reagent dispensing section which adds reagent to a sample that has been aspirated by the sample aspirating apparatus; and a detecting section which optically detects a component contained in the mixture of the sample and reagent.

PREFERRED EMBODIMENTS

The embodiments are described hereinafter based on the drawings.

The structure of a sample analyzer 1 provided with a first sample dispensing arm of an embodiment of the present invention is first described below with reference to FIGS. 1 through 10, and FIGS. 10, 14, and 16. Note that the present embodiment pertains to the present invention applied to a sample dispensing arm of a sample analyzer as an example of the sample aspirating apparatus of the present invention.

The analyzer 1 is a blood coagulation analyzer which optically measures and analyzes samples by irradiating with light a measurement sample prepared by adding reagent to a sample (blood plasma) using coagulation, synthetic substrate, immunoturbidity, and agglutination methods.

Figure 1:
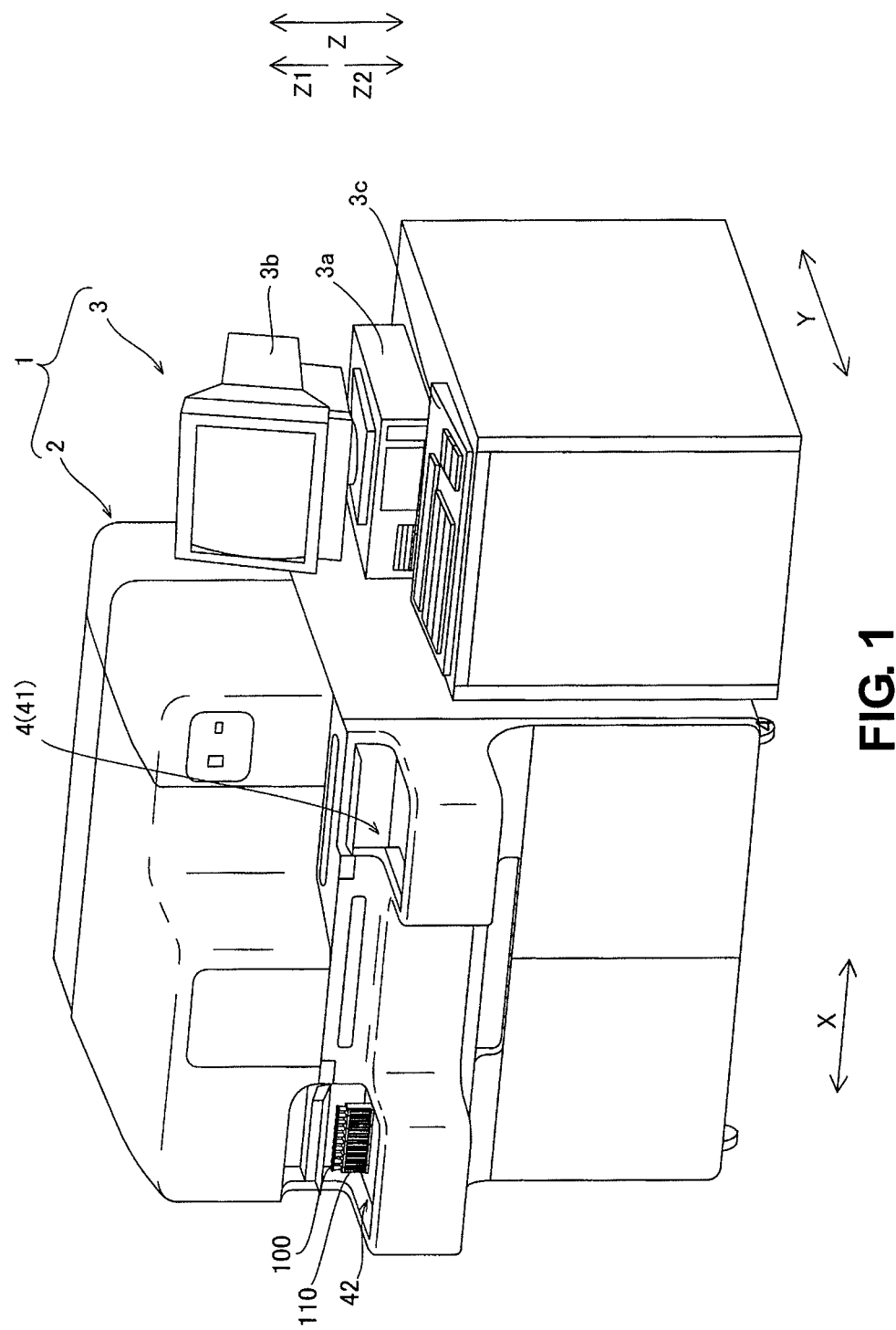
FIG. 1 is a perspective view showing the general structure of a sample analyzer with a first sample dispensing arm of an embodiment of the present invention.

As shown in FIG. 1, the analyzer 1 has a measuring device 2 which optically measures the components in the sample (blood plasma), and a control device 3 configured by a PC (personal computer) which is electrically connected to the measuring device 2. The control device 3 is a computer mainly having a controller 3a, display 3b, and keyboard 3c. The control device 3 has the functions of transmitting to the measuring device 2 the start and end instructions for the sample analysis operation based on operation input, and receiving analysis results and various reports such as error reports and drive stop report from the measuring device 2. The control device 3 also has the function of displaying on the display 3b the obtained analysis results based on the detection values of the measuring device 2 and the received error reports.

Figure 2:
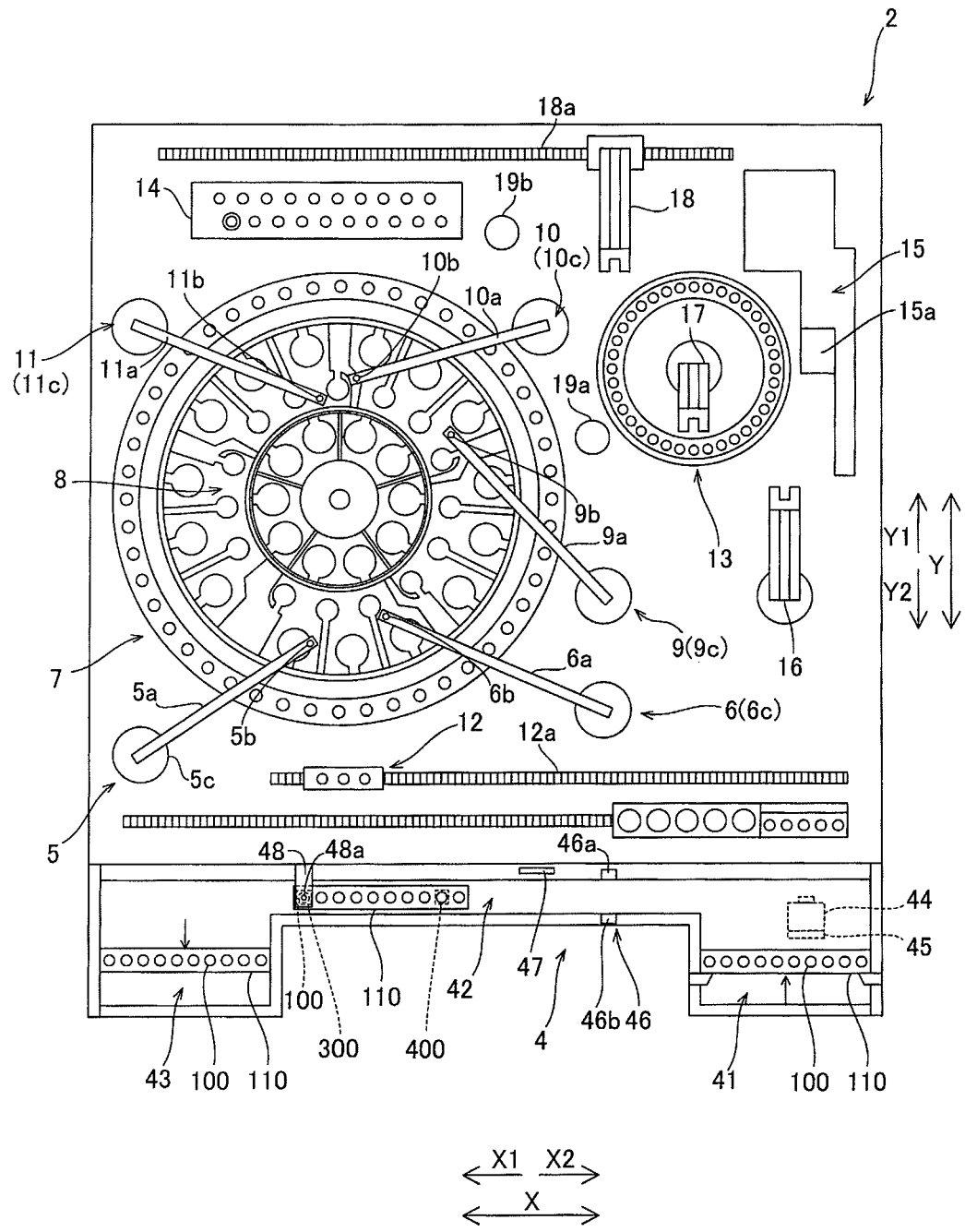
FIG. 2 is a top view showing the general structure of a sample analyzer with a first sample dispensing arm of an embodiment of the present invention.

As shown in FIG. 2, the measuring device 2 incorporates a sample transporter (sampler) 4, first sample dispensing arm 5, second sample dispensing arm 6, cuvette (reaction vessel) unit 7 and reagent unit 8, reagent dispensing arms 9, 10, and 11, cuvette transporter 12, reactor 13, detecting unit 14, cuvette supplier 15, and catcher units 16, 17, and 18.

The sample transporter 4 has a rack storage 41, rack transporter 42, and rack collector 43. The rack storage 41 has the functions of storing the racks 110 (refer to FIG. 1) that are loaded with a plurality of sample containers 100 accommodating samples, and moving the rack 110 to the track transporter 42. The rack transporter 42 has a servo motor 44 and an encoder 45, and is disposed so as to extend in the X direction across the rack storage 41 and rack collector 43. The rack transporter 42 is configured to move the rack 110 to an optional position on the rack transport 42 extending in the X direction by driving a feed mechanism not shown in the drawing via the servo motor 44. Thus, the rack transporter 42 moves the sample container 100 to be analyzed (dispensing object) loaded in the rack 110 to the sample aspirating position of the first sample dispensing arm 5 and the sample aspirating position 400 of the second sample dispensing arm 6. The rack collector 43 has the function of collecting the rack 110 holding the sample container 100 that has been used for dispensing to the rack transporter 42.

Figure 3:
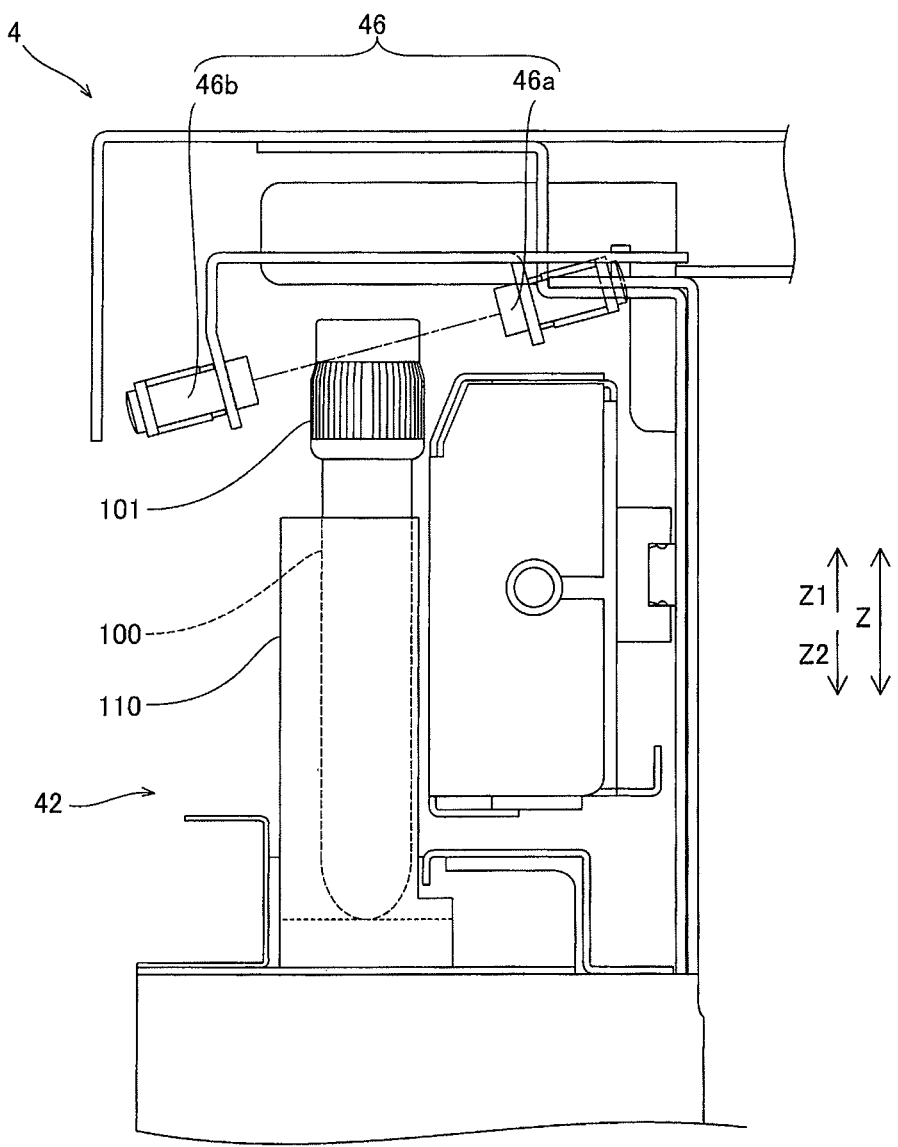
FIG. 3 is a partial cross sectional view showing the cap sensor of the sample transporting section in the sample analyzer of FIG. 2.

The rack transporter 42 has a cap sensor 46, barcode reader 47, and pipette washing unit 48 disposed along the X direction. As shown in FIG. 3, the cap sensor 46 is an optical sensor having a light emitter 46a and a light receiver 46b which are disposed so that the cap 101 on the top end (end in the arrow Z1 direction) of the sample container 100 in the rack 110 transported by the rack transporter 42 pass through the light path between the light emitter 46a and the light receiver 46b. The sample container 100 is a tube-like container with an opening at the top end, and either a sample container (refer to FIG. 14) sealed via a cap 101 over the opening at the top end, or a sample container (refer to FIG. 16) without a cap 101 may be used. The cap sensor 46 operates by the irradiating light from the light emitter 46a toward the light receiver 46b while the sample container 100 is between the light emitter 46a and the light receiver 46b. When the light is not received by the light receiver 46b, the cap 101 is detected on the sample container 100. Alternatively, when the light is received by the light receiver 46b, the absence of a cap 101 is detected on the sample container 100. Hence, the presence or absence of a cap can be quickly detected for each sample container by detecting the presence or absence of the cap on the sample containers 100 being transported by the rack transporter 42 even when capped sample containers 100 and uncapped sample containers 100 (refer to FIG. 16) are mixed in the rack 110.

As shown n FIG. 2, the barcode reader 47 has the function of reading the identification barcode label (not shown) adhered to the rack 110 transported by the rack transporter 42, and reading the identification barcode label (not shown) adhered to the sample containers 100 in the rack 110.

Figure 5:
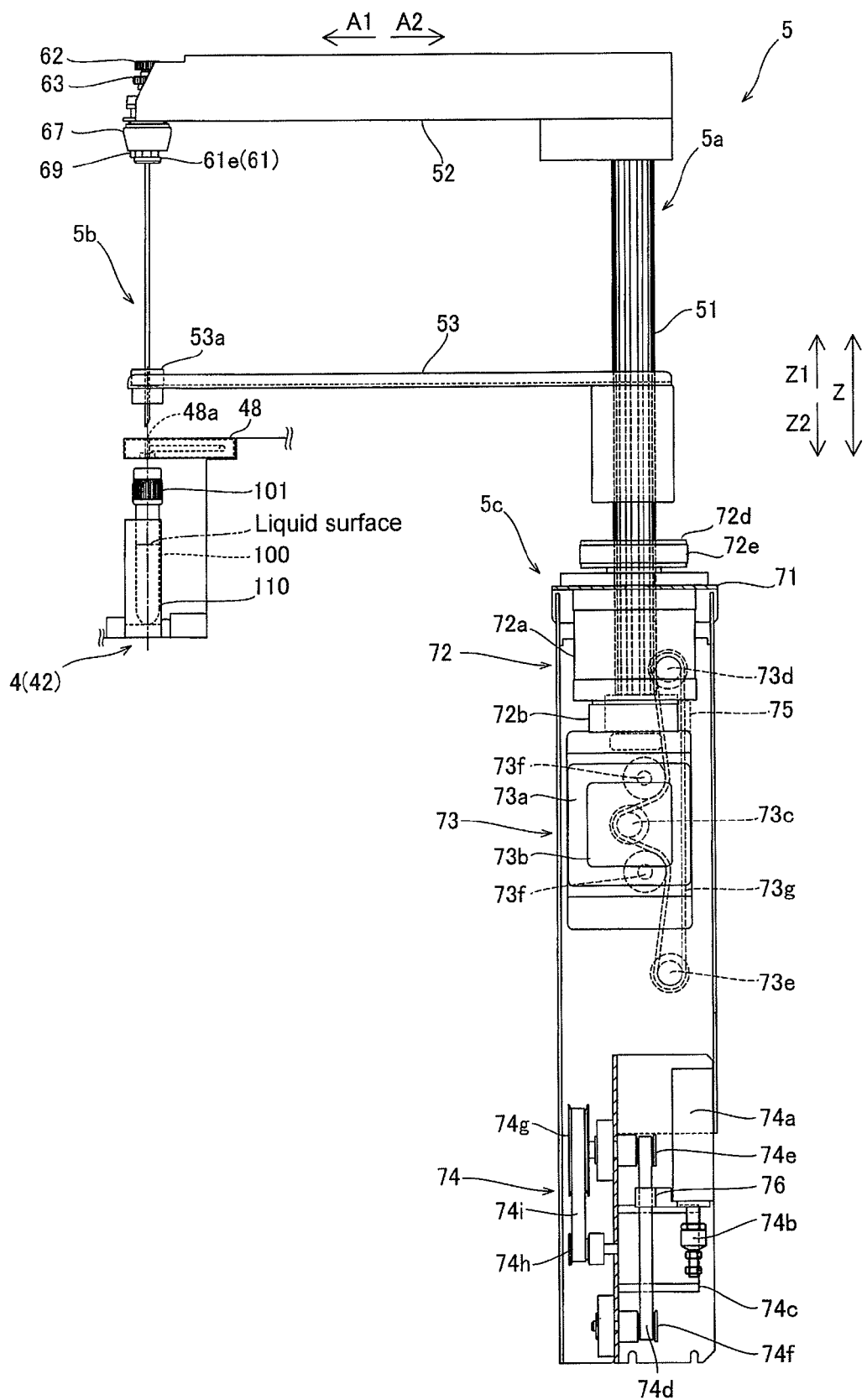
FIG. 5 is a side view schematically showing the first sample dispensing arm of the embodiment of the present invention.

The pipette washing unit 48 is disposed at a position above the sample aspirating position 300 of the rack transporter 42 (refer to FIG. 5). The pipette washing unit 48 has a vertical (Z direction) pipette path 48a, so that the pipette 5b (described later; refer to FIG. 5) of the first sample dispensing arm 5 passes through the pipette path 48a when aspirating a sample from the sample container 100. The pipette washing unit 48 has the function of washing the pipette 5b via the pipette 5b aspirating and discharging the washing liquid as it passes through the interior of the pipette path 48a. The pipette washing unit 48 is vertically movable. The pipette washing unit 48 is raised by the controller 3a via driving a motor (not shown). The washing unit 48 has the function of pressing downward on the cap 101 of the sample container 100 via the vertical movement of the washing unit. There is no backlash to the sample container 100 when the pipette 5b (6b) provided on the first sample dispensing arm 5 (second sample dispensing arm 6) penetrates the cap 101. Bouncing of the sample container 100 caused by the rising pipette is also prevented when the pipette 5b which has penetrated the cap 101 is extracted therefrom.

In the present embodiment, the first sample dispensing arm 5 has an arm 5a, pipette 5b, and body 5c, and has the function of aspirating the sample within the sample container 100 transported to the sample aspirating position 300 by the sample transporter 4, and dispensing (discharging) the aspirated sample to a cuvette placed on the cuvette transporter 12 or a cuvette placed on the cuvette unit 7. Note that the detailed structure of the first sample dispensing arm 5 is described later.

The second sample dispensing arm 6 has an arm 6a, pipette 6b, and body 6c, and has the function of aspirating the sample within the sample container 100 transported to the sample aspirating position 400 by the sample transporter 4, and dispensing (discharging) the aspirated sample to a cuvette placed on the cuvette transporter 12 or a cuvette placed on the cuvette unit 7.

The reagent unit 8 is provided to hold the reagent containers filled with various types of reagent, such as reagent and dilution liquid, used in measurements.

The reagent dispensing arms 9, 10, and 11 have the function of aspirating the reagent in the reagent container (not shown) disposed on the reagent unit 8, and discharging the predetermined reagent to a cuvette disposed on either the cuvette unit 7, cuvette transporter 12 or the like. The reagent dispensing arms 9, 10, and 11 respectively have an arm 9a, 10a, and 11a, pipette 9b, 10b, and 11b, and body 9c, 10c, and 11c. The reagent dispensing arm 9, 10, 11) is configured so that the body 9c (10c, 11c) rotates the arm 9a (10a, 11a) so that the pipette 9b (10b, 11b) is positioned above the reagent container and above the cuvette, and the body 9c (10c, 11c) raises the arm 9a (10a, 11a) to aspirate and discharge the reagent from the pipette 9b (10b, 11b).

The cuvette transporter 12 is configured to hold the cuvette placed in the unit in the X direction on the transport path 12a. The cuvette transporter 12 has the function of moving the placed cuvette to a dispensing position in front of the cuvette unit 7 and a transport position in front of the cuvette unit 16.

The reactor 13 is annular in shape to surround the catcher unit 17, and is configured to hold several cuvettes. The reactor 13 has the function of heating the placed cuvette. That is, the mixture of the sample and reagent in the cuvette is heated in the reactor 13 to promote a reagent between the type of reagent and the sample in the cuvette The detecting unit 14 has the function of detecting optical information of the reaction of the components in the measurement sample by performing optical measurements of the measurement sample after the sample is reacted with the types of reagents in the reactor 13.

The cuvette supplier 15 houses a plurality of cuvettes, and sequentially supplies cuvettes to the cuvette reservoir 15a.

The catcher units 16, 17, and 18 respectively have the functions of holding and moving the cuvettes. The catcher unit 16 places the cuvette from the cuvette reservoir 15a on the cuvette transporter 12, and moves the cuvette from the transporter 12 to the reactor 13. The catcher unit 18 is movable in the X direction on the transport path 18a, and has the function of moving the cuvette from the reactor 13 to the detecting unit 14. The catcher units 17 and 18 respectively have the function of disposing of the used cuvette via the disposal ports 19a and 19b.

Figure 4:
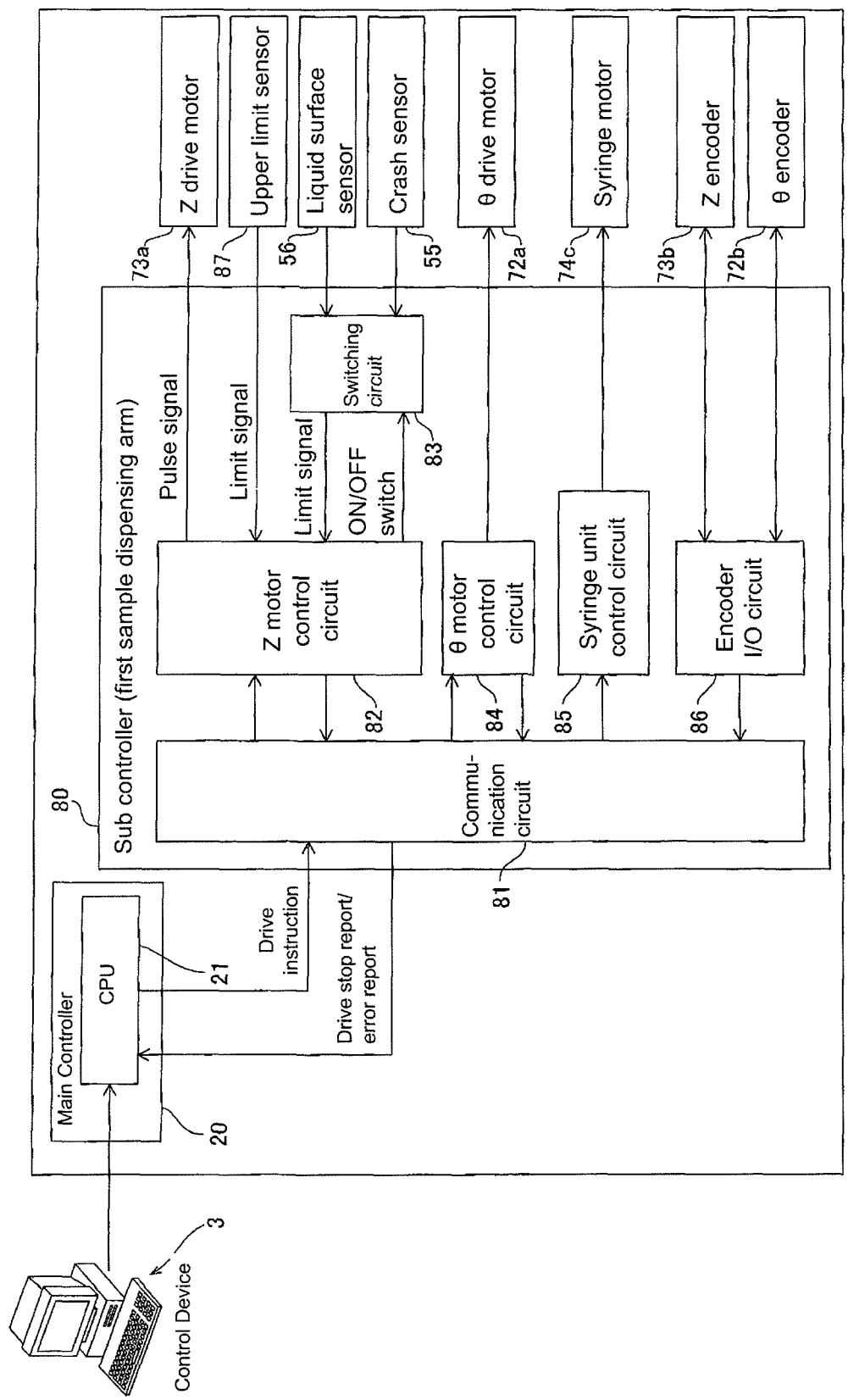
FIG. 4 is a block diagram showing the controller of a sample analyzer with the first sample dispensing arm of an embodiment of FIG. 1.

As shown in FIG. 4, the measuring device 2 has a main controller 20, and sub controllers (only the sub controller 80 of the first sample dispensing arm 5 is shown in FIG. 4) for performing operational controls of various devices (various dispensing arms such as the first sample dispensing arm 5, reactor 13, reagent unit 8, catcher units 16 through 18 and the like). The devices such as each type of dispensing arm, reactor 13, cuvette unit 7, reagent unit 8, cuvette transporter 12, catcher units 16 through 18 are respectively controlled by sub controllers based on drive instructions from the main controller 20. The sample transporter 4 is also controlled by the main controller 20.

The main controller 20 has a CPU 21 as shown in FIG. 4. The main controller 20 is connected to the control device 3, and has the functions of transmitting the sample optical information (measurement data) to the control device 3, and receiving signals from the controller 3a (refer to FIG. 1) of the control device 3. The main controller 20 also has the functions of transmitting drive instruction from the CPU 21 to each part of the sample transporter 4 and the measuring device 2, and receiving error reports and drive stop reports of each part. The received error reports and drive stop reports of each part are transmitted from the main controller 20 to the control device 3.

Details of the structure of the first sample dispensing arm 5 of the present embodiment are described below. The sub controller 80 of the first sample dispensing arm 5 is also described below. Note that only the sub controller 80 of the first sample dispensing arm 5 in the present embodiment is described, and other sub controllers are omitted.

As shown in FIG. 2, after the first sample dispensing arm 5 disposes the pipette 5b (refer to FIG. 14) above the sample aspirating position 300 by rotating the arm 5a via the body 5c, the pipette 5b is inserted in the sample container 100 disposed at the sample aspirating position 300 when the body 5c lowers the pipette 5b to aspirate the sample as shown in FIG. 5. The first sample dispensing arm 5 retracts the pipette 5b from the sample container 100 by raising the arm 5a, the rotates the arm 5a to position the pipette 5b at the dispensing position above the cuvette disposed at the cuvette unit 7 or the cuvette transporter 12, and dispenses (discharges) the sample therein.

Figure 6:
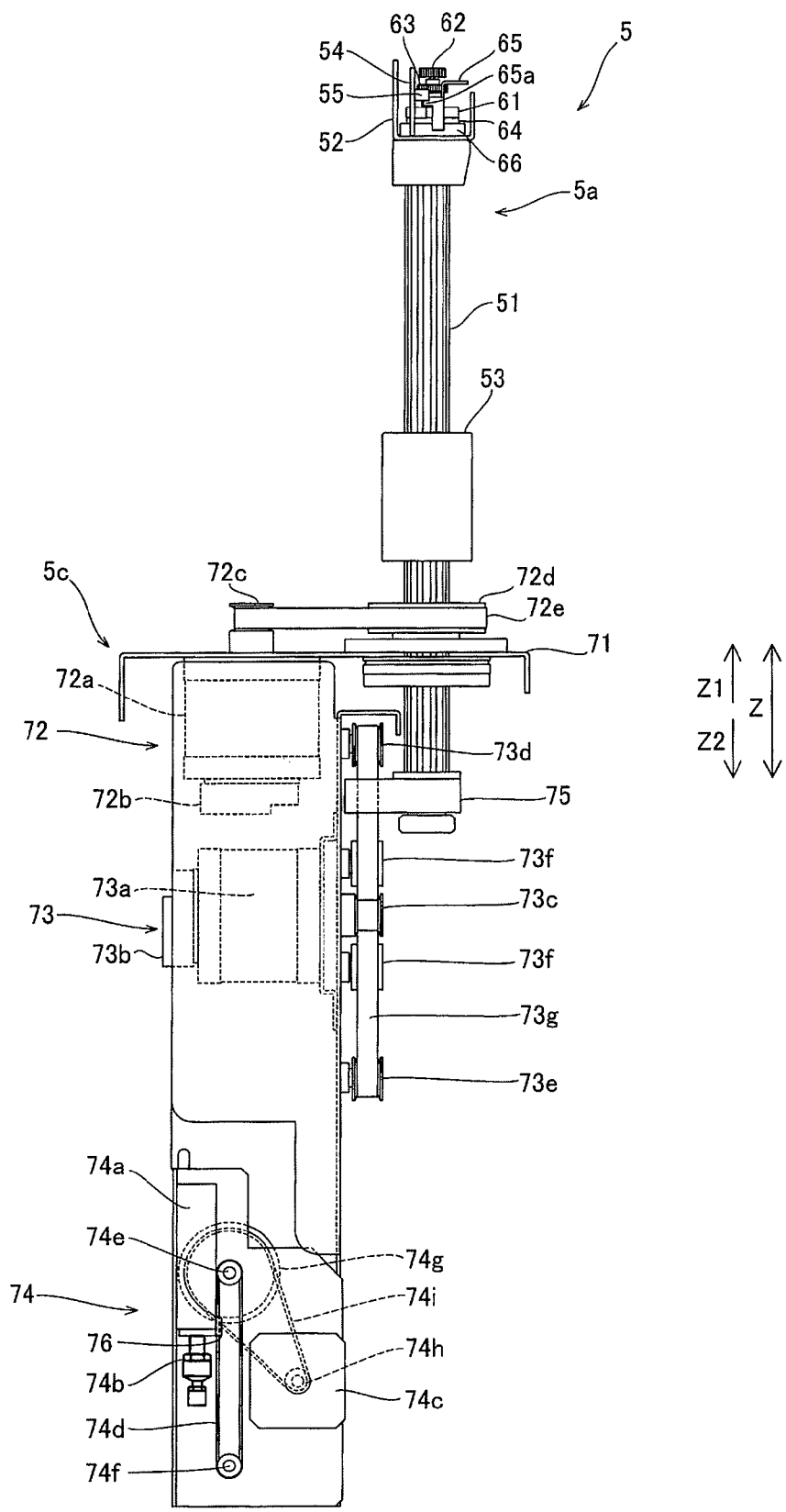
FIG. 6 is a rear view schematically showing the first sample dispensing arm of the embodiment of FIG. 5.
Figure 7:
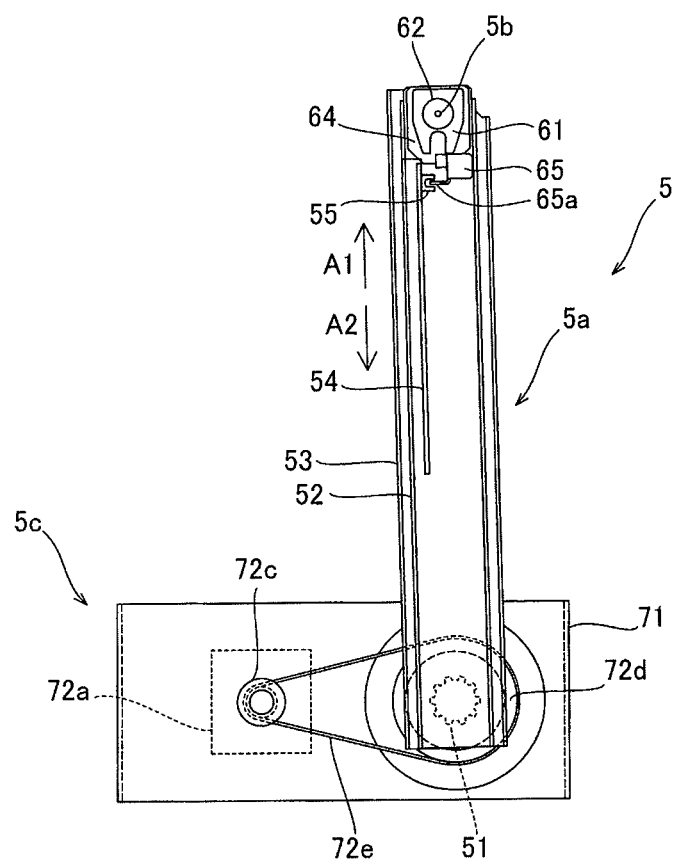
FIG. 7 is a top view schematically showing the first sample dispensing arm of the embodiment of FIG. 5.

As shown in FIGS. 5 through 7, the arm 5a has a shaft 51, support member 52, and guide 53. The arm 5a is configured to rotate and rise in its entirety including the shaft 51, support member 52, and guide 53 via the θ drive motor 72a and the Z drive motor 73a of the body 5c. The support member 52 is fixed to the top end of the shaft 51 which is supported so as to be rotatable and capable of rising around the body 5c. The shaft 51 is a hollow spline shaft, and is configured so that a wiring process such as the signal wiring of the various sensors and a tube (not shown) connected to the pipette 5b pass through the interior of the shaft 51.

The support member 52 has an approximately U-shaped cross section (refer to FIG. 6) and is formed of a metal plate extended horizontally, and is mounted on the tip of the shaft 51 at the base (on the side in the arrow A2 direction). At the tip (side in the arrow A1 direction) of the support member 52, the pipette 5b extends downward and is mounted so as to be movable relative to the support member 52. As shown in FIG. 7, the support member 52 has a control substrate 54 provided with the sub controller 80 (refer to FIG. 4) of the first sample dispensing arm 5. The control substrate 54 is provided with an optical type crash sensor 55 which has a light emitting part and a light receiving part. As will be described later, the crash sensor 55 detects the raising of the pipette 5b relative to the support member 52 by detecting a detection piece 65a of the detected member 65 which moves together with the pipette 5b. The control substrate 54 is provided with a capacitance type liquid surface sensor 56 (refer to FIG. 4) which uses the pipette 5b as an electrode so as to detect when the tip of the pipette 5b contacts the liquid surface.

As shown in FIG. 5, the guide 53 is disposed below and parallel to the support member 52. The base of the guide 53 is fixedly mounted on the shaft 51. A pipette guide 53a which has a through hole in the vertical direction (direction) is provided on the tip of the guide 53, and mounted with the pipette 5b in the inserted state. Thus, the pipette 5b is guided downward (arrow Z direction). 2

Figure 8:
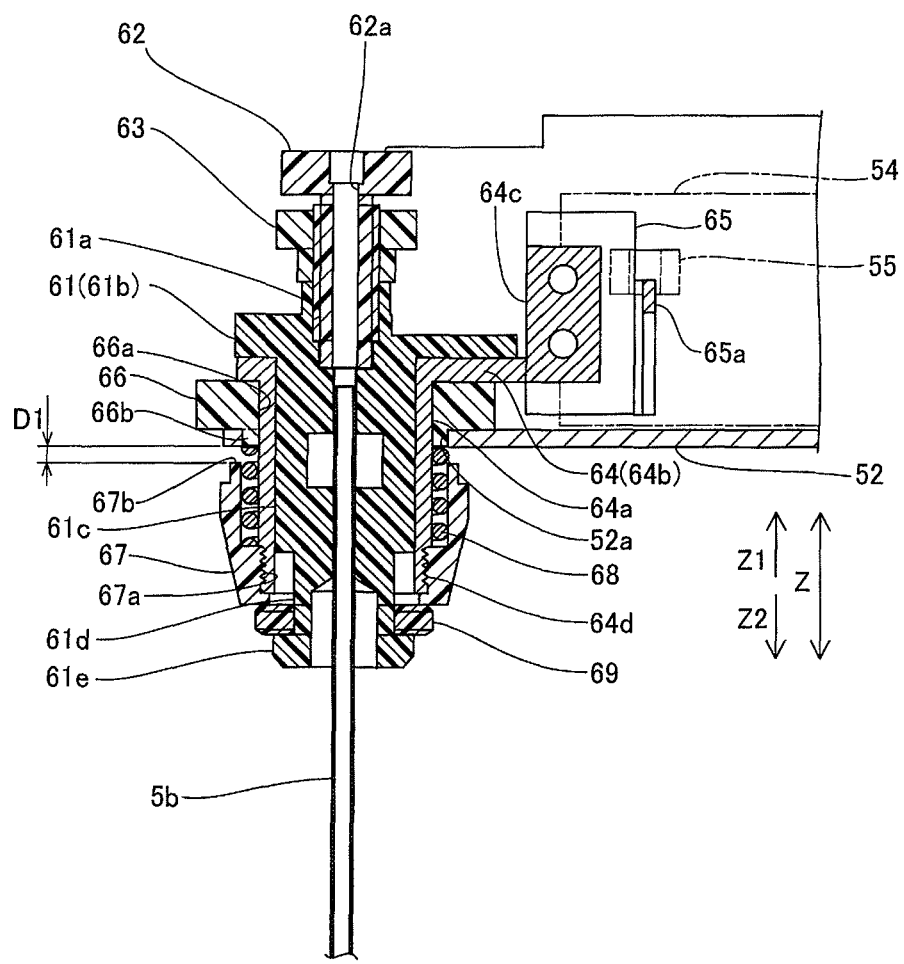
FIG. 8 is a cross sectional view illustrating the pipette mounting structure of the first sample dispensing arm of the embodiment of FIG. 5.
Figure 9:
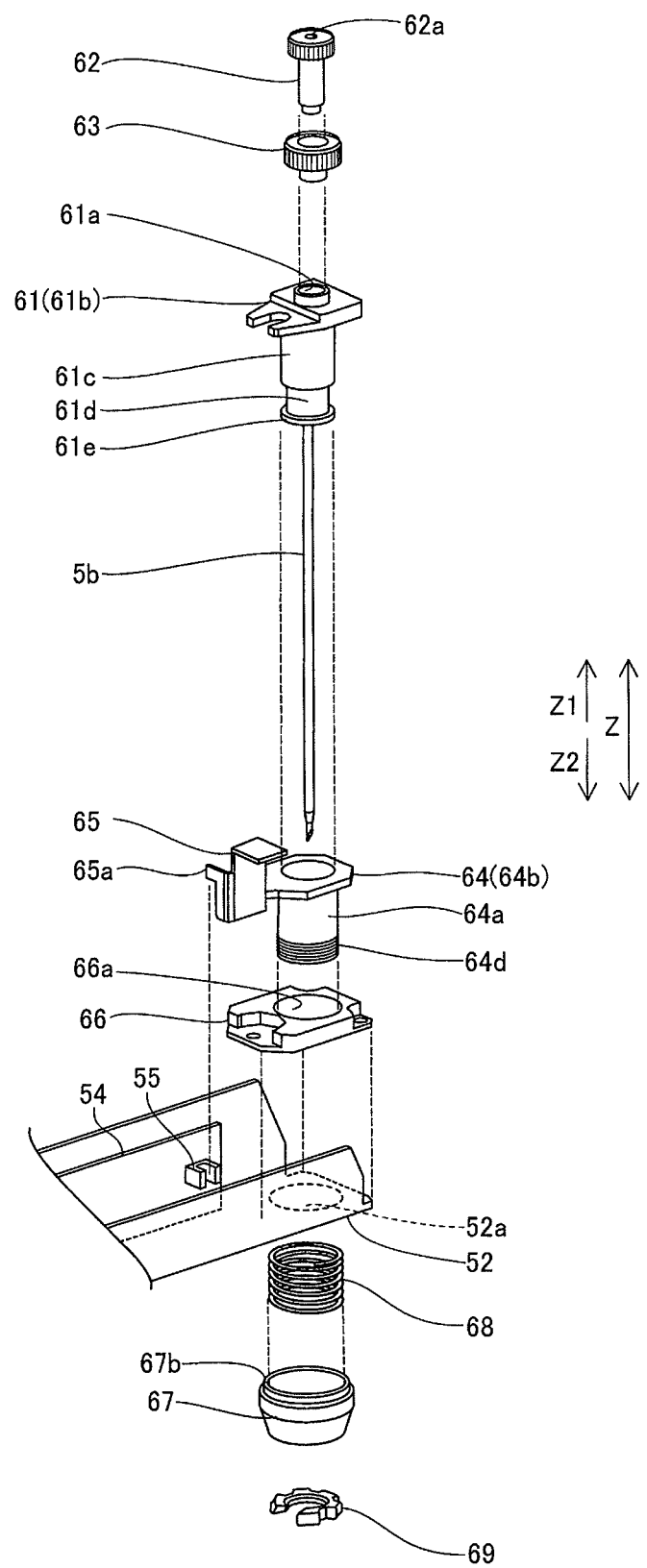
FIG. 9 is an exploded perspective view illustrating the pipette mounting structure of the first sample dispensing arm of the embodiment of FIG. 8.

The pipette 5b is a metal tubular member, mounted facing downward from the support member 52. The pipette 5b forms an acute angle so the tip (bottom end) passes through the cap 101 of the sample container 100. During aspiration of the sample in the sample container 100, the pipette 5b is lowered by lowering the support member 52 (arm 5a), and the tip of the pipette 5b is inserted into the sample container 5b by passing through the cap 101 from above. As shown in FIGS. 8 and 9, the 5b is supported by the retaining member 61 so as to be inserted into the hollow holding member 61.

The retaining member 61 has a top part 61b with an aperture 61a which communicates with the tip of the pipette 5b, a cylindrical first barrel 61c extending downward from the top part 61b, a cylindrical second barrel 61d extending downward from the first barrel 61c, and a flange 61e extending laterally from the second barrel 61d.

At the aperture 61a at the tip of the retaining member 61 is mounted a hollow connecting member 62 with a flow path 61a, and a connecting member 63 for fixedly attaching the connecting member 61. The pipette 5b, retaining member 61, and flow path 62a of the connecting member 62 are configured to communicate. One end of a tube (not shown) is mounted on the tip of the flow path 62a of the connecting member 62, and the other end of the tube passes through the interior of the shaft 51 and is connected to a syringe pump unit 74 (refer to FIG. 5) which is described later. When the syringe pump 74 applies a negative pressure to the pipette 5b, the sample is aspirated by the tip of the pipette 5b. When the syringe pump 74 applies a positive pressure to the pipette 5b, the aspirated sample is discharged from the tip of the pipette 5b. The retaining member 61 is supported by an oscillating member 64 while the first barrel 61c is inserted in the barrel 64a of the oscillating member 64. Thus, the pipette 5b and the retaining member 61 can be integratedly reseated relative to the oscillating member 64.

The oscillating member 64 is a metal member having a barrel 64a, support 64b, and mount 64c. The barrel 64a is cylindrically shaped and extends downward from the support 64b, and has a threaded part 64d on the outer surface near the bottom end. The support 64b supports the retaining member 61 by the top surface of the support 64b abutting the bottom surface of the top part 61b of the retaining member 61. A detected member 65 is mounted on the mount 64c. the detected member 65 is disposed opposite the control substrate 54 (refer to FIG. 7) provided with the crash sensor 55. the detected member 65 is integratedly provided with a detection piece 65a which extends to the opposed crash sensor 55 side. When the oscillating member 64 is moved upward (arrow Z1 direction; refer to FIG. 10), the detection piece 65a blocks the crash sensor 55. The oscillating member 64 is supported so as to be upwardly movable and the barrel 64a can be inserted into the guide member 66. Note that the barrel 64a is disposed so as to protrude to the bottom side (side in the arrow Z2 direction) of the support member 52 through the mounting hole 52a of the support member 52 and the guide member 66. The threaded part 67a of an engaging member 67 is screwed to the threaded part 64d on the bottom side of the support member 52.

The guide member 66 has a guide surface 66a configured by the inner surface of a circular hole for the insertion of the barrel part 64a of the oscillating member 64, and a projecting part 66b extending downward from the bottom surface. The guide member 66 supports the upward movement (oscillation) of the oscillating member 64 when the top surface of the guide member 66 abuts the bottom surface of the support 64b of the oscillating member 64. The oscillating member 64 is guided so as to be upwardly (arrow Z1 direction) movable when the exterior surface of the barrel part 64a abuts the guide surface (inner surface) 66a of the guide member 66. The guide member 66 is positioned so that the projecting part 66b is fitted in the mounting hole 52a of the support member 52, and fixedly attached to the support member 52 by a screw or the like.

Figure 10:
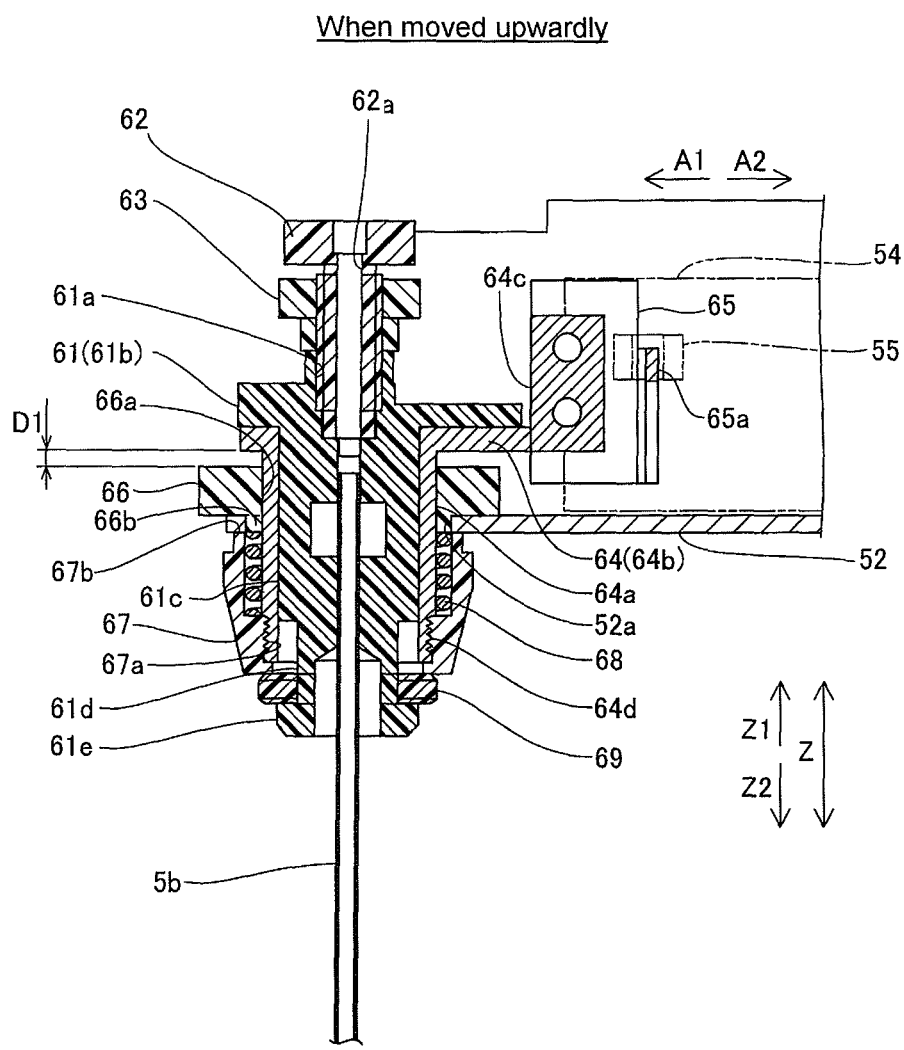
FIG. 10 is a cross sectional view showing the pipette of the first sample dispensing arm of FIG. 8 when raised relative to the support member.

The engaging member 67 has a cylindrical shape, and is mounted on the oscillating member 64 by screwing the threaded part 67a formed on the bottom part of the inner surface of the engaging member 67 to the threaded part 64d of the barrel part 64a of the oscillating member 64. The engaging member 67 is configured so that the top end surface 67b of the engaging member 67 is separated by a predetermined distance D1 from the bottom surface of the support member 52. The distance D1 is, for example, 1.5 mm. As shown in FIG. 10, the engaging member 67 therefore has the function of engaging the oscillating member 64 when engaging member 67 is integratedly moved upward (arrow Z1 direction) a distance of D1 with the oscillating member 64 so that the top end surface 67b of the engaging member 67 abuts the bottom surface of the support member 52. Therefore, the upward movable distance of the oscillating member 64 relative to the guide member 66 (support member 52) is restricted to the distance D1 via the engaging member 67. A coil spring 68 is also provided between the inner surface of the engaging member 67 and the outer surface of the barrel part 64a of the oscillating member 64.

The spring coil 68 is housed within the engaging member 67 when inserted barrel part 64a of the oscillating member 64. The bottom end of the coil spring 68 abuts the top surface on the inner side of the engaging member 67, and the top end of the coil spring 68 abuts the bottom surface of the support member 52 (bottom surface of the projecting part 66b of the guide member 66). Therefore, the coil spring 68 is compressedly and elastically deformed between the bottom surface of the support member 52 and the top inner surface of the engaging member 67 in conjunction with the upward movement of the oscillating member 64 (engaging member 67; refer to FIG. 10). The coil spring 68 is thus configured to exert a downward repulsive force (exerted force) on the oscillating member 64 (engaging member 67) when the oscillating member 64 moves upward.

As shown in FIG. 8, the flange 61e and part of the second barrel part 61d of the retaining member 61 protrude downward (arrow Z2 direction) from the bottom end of the engaging member 67 when the retaining member 61 is supporting the oscillating member 64. A spacer 69 is mounted on the second barrel part 61d so as to abut the top surface of the flange 61e and the bottom end surface of the engaging member 67. Hence, the retaining member 61 engages the bottom surface side of the engaging member 67 through the spacer 69, and the bottom surface of the top part 61b engages the top surface of the support part 64b of the oscillating member 64. As a result, the pipette 5b held by the retaining member 61 moves upward (arrow Z1 direction) integratedly with the oscillating member 64 via the support member 52 (and guide member 66).

According the present embodiment having this structure, when the pipette 5b (arm 5a) is lowered and the tip of the pipette 5b comes into contact with the cap 101 of the sample container 100 of another object, the coil spring 68 is elastically compressed and the pipette 5b is moved upward only a distance D1 relative to the support member 52, as shown in FIG. 10. When the pipette 5b is moved upward only a distance D1 relative to the support member 52, the upward movement of the pipette 5b is detected when the detection piece 65a of the detected member 65 mounted on the oscillating member 64 blocks the crash sensor 55. When the pipette 5b is retracted from the cap 101 or other object, the pipette 5b is naturally returned to the pre-collision position via the coil spring 68.

As shown in FIGS. 5 and 6, the body 5c has a chassis 71 which supports the shaft 51 so as to be rotatable and liftable, rotation device 72 which rotates the shaft 51 (arm 51a), elevator device 73 which raises and lowers the shaft 51 (arm 51a), and syringe pump unit 74 which provides positive and negative pressures to aspirate and discharge the sample from the pipette 5b. The chassis 71 supports the shaft 51 so as to be rotatable and vertically movable.

The rotation device 72 has a θ drive motor 72a which is a step motor, and a θ encoder 72b which detects the rotational position of the θ drive motor 72a. As shown in FIGS. 6 and 7, pulleys 72c and 72d are mounted on the output shaft of the shaft 51 and the θ drive motor 72a, respectively. Note that the pulley 72d engages the rotational direction around the shaft 51, which is a spline shaft, and is mounted so as to be supported by the chassis 71 and relatively movable in vertical directions (Z directions). A drive belt 72e is looped on the pulleys 72c and 72d. Hence, the arm 5a is rotated around the shaft 51 by the θ drive motor 72a.

As shown in FIG. 5, the elevator device 73 has a Z drive motor 73a which is a step motor, and a Z encoder 73b which detects the rotational position of the Z drive motor 73a. A drive belt 73g is looped around the pulley 73c mounted on the output shaft of the Z drive motor 73a, and the pair of pulleys 73d and 73e disposed in vertical (Z directions) alignment with the chassis 71 through a tension pulley 73f. A coupling 75 (refer to FIG. 6) for connecting the drive belt 73g and the shaft 51 is provided at a position between the pair pf pulleys 73d and 73e. Hence, the arm 5a (pipette 5b) can be raised and lowered vertically by raising and lowering the drive belt 73g via the Z drive motor 73a.

The syringe pump unit 74 has a syringe 74a and plunger 74b, and a syringe motor 74c which advances and retracts the plunger 74b. A tube (not shown) is connected to the syringe 74a, and communicates with the pipette 5b (connecting member 62) through the interior of the shaft 51. The syringe unit 74 is provided with a pair of pulleys 74e and 74f around which is looped a drive belt 74d along the advance and retract directions (vertical directions) of the plunger 74b, and the drive belt 74d and plunger 74b are connected by a coupler 76. The pulley 74e is connected to the pulley 74g, and a drive belt 74i is looped around the pulley 74g and a pulley 74h on the output side of the syringe motor 74c. Thus, the plunger 74b is advanced and retracted relative to the syringe 74a by the drive of the syringe motor 74c, such that a sample can be aspirated and discharged from the pipette 5b by exerting positive and negative pressures on the pipette 5b.

As shown in FIG. 4, the sub controller 80 of the first sample dispensing arm 5 is provided with a communication circuit 81, Z motor control circuit 82, switching circuit 83, θ motor control circuit 84, syringe pump unit control circuit 85, and encoder I/O circuit 86.

The communication circuit 81 performs communications with the main controller 20, receives drive instructions (Z direction drive instruction, rotational (θ) direction drive instruction, syringe pump unit 74 drive instruction) for the first sample dispensing arm 5 in conjunction with the analysis operation from the CPU 21 of the main controller 20, and transmits error reports and drive stop reports of the first sample dispensing arm 5 to the main controller 20. The communication circuit 81 also outputs the received drive instructions to the motor control circuit 82, θ motor control circuit 84, and syringe pump unit control circuit 85, respectively.

The Z motor control circuit 82 has the functions of outputting pulse signals in response to the Z direction drive instructions to the Z drive motor 73a, and controlling the raising and lowering of the arm 5a (pipette 5b) via the Z drive motor 73a. The Z motor control circuit 82 receives a limit signal from the upper limit sensor 87 (shown only in FIG. 4) which detects the upper limit position of the arm 5a, and receives the limit signal (detection signal) from the crash sensor 55 and liquid surface sensor 56 through the switching circuit 83. When the limit signal (detection signal) is received during the actuation of the Z drive motor 73a, the Z motor control circuit 82 stops the output of the pulse signals to the Z drive motor 73a. As a result, the actuation of the Z drive motor 73a stops.

Note that the sub controller 80 is an FPGA (field programmable gate array). The Z motor control circuit 82 is a hardware circuit configured by an FPGA, and the output of the pulse signal is stopped at the moment the limit signal is latched. Therefore, stopping the actuation of the Z drive motor 73a is accomplished without waiting for a determination by the main controller 20, and the main controller 20 only receives a drive stop report indicating that the actuation of the Z drive motor 73a has been stopped. Therefore, the lowering of the pipette 5b is quickly stopped at crash by stopping the actuation of the Z drive motor 73a instantly via a hardware circuit without waiting for a determination by the main controller 20 which is a CPU. The Z motor control circuit 82 also outputs an ON/OFF switching signal to the switching circuit 83 based on the control signal from the CPU 21 of the main controller 20.

The switching circuit 83 has the functions of receiving the detection signals (limit signals) of the liquid surface sensor 56 and the crash sensor 55, and outputting the received limit signals to the Z motor control circuit 82. The switching circuit 83 switches to block one or both outputs of the detection signals (limit signals) of the liquid surface sensor 56 and crash sensor 55 based on the ON/OFF signal from the Z motor control circuit 82 in response to instruction from the main controller 20. The main controller 20 switches the crash sensor 55 ON/OFF and switches the liquid surface sensor 56 ON/OFF by controlling the limit circuit 83.

When the main controller 20 transmits an instruction to turn OFF the crash sensor 55 to the Z motor control circuit 82, the Z motor control circuit 82 transmits a switching signal (switch OFF signal) to the switching circuit 83 to block the output of the limit signals of the crash sensor 55 to the Z motor control circuit 82. When the switch OFF signal is received, the switching circuit 83 blocks the output of the limit signal of the crash sensor 55 to the Z motor control circuit 82 until a switch ON signal (described later) is received. The main controller 20 executes an identical process to turn OFF the liquid surface sensor 56.

When the main controller 20 transmits an instruction to turn ON the crash sensor 55 to the Z motor control circuit 82, the Z motor control circuit 82 transmits a switching signal (switch ON signal) to the switching circuit 83 to allow the output of the limit signals of the crash sensor 55 to the Z motor control circuit 82. When the switch ON signal is received, the switching circuit 83 allows the output of the limit signal of the crash sensor 55 to the Z motor control circuit 82 until a switch OFF signal is received. The main controller 20 executes an identical process to turn ON the liquid surface sensor 56.

When the switching circuit 83 blocks the output of the limit signal to the Z motor control circuit 82, the Z motor control circuit 82 (sub controller 80) controls the actuation of the Z drive motor 73a regardless of whether the crash sensor 55 has detected a collision of the pipette 5b with an obstacle, or the liquid surface sensor 56 has detected the pipette 5b at the liquid surface.

The θ motor drive circuit 84 has the functions of outputting pulse signals to the θ drive motor 72a in response to rotational (θ) drive instructions, and controls the operation of the rotation (rotation around the shaft 51) of the arm 5a via the θ drive motor 72a.

The syringe pump unit control circuit 85 has the function of controlling the drive operation of the syringe motor 74c in response to the drive instruction (aspiration or discharge) of the syringe pump unit 74.

The encoder I/O circuit 86 has the functions of receiving the output signals (rotational position information of the Z drive motor 73a) from the Z encoder 73b and the output signals (rotational position information of the θ drive motor 72a) from the θ encoder 72b, and outputting these received signals to main controller 20 through the communication circuit 81. Thus, the movement (movements in the vertical direction and rotational direction) of the arm 5a according to the drive instruction from the main controller 20 can be confirmed, and the pipette 5b can be accurately positioned above the sample aspirating position 300.

Note that the main controller 20 similarly transmits the drive instruction to the servo motor 44 (refer to FIG. 2) of the sample transporter 4, and receives the output signals (servo motor 44 rotational position information) from the encoder 45 (refer to FIG. 2). Hence, the sample can be aspirated since the sample container 100 to be aspirated is held in the rack 110 transported by the sample transporter 4 and accurately positioned at the sample aspirating position 300 (400).

The sample dispensing operation performed by the first sample dispensing arm 5 of the present embodiment is described below with reference to FIGS. 2 through 5 and FIGS. 11 through 14. The operation of the first sample dispensing arm 5 described below is accomplished by controlling the various drive motors (Z drive motor 73a, θ drive motor 72a, syringe motor 74c) via the control circuits (Z motor control circuit 82, θ motor control circuit 84, syringe pump unit control circuit 85) of the sub controller 80 based on the drive instructions transmitted from the main controller 20 (CPU 21) to the sub controller 80.

Figure 11:
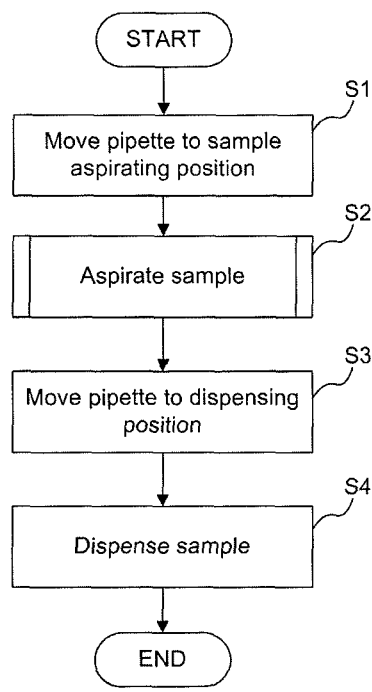
FIG. 11 is a flow chart illustrating the sample dispensing process during the operation of the first sample dispensing arm of the embodiment of the present invention.

In step S1 of FIG. 11, the pipette 5b is first moved above the sample aspirating position 300. That is, the θ drive motor 72a rotates the arm 5a until the pipette 5b is above the sample aspirating position 300. As shown in FIG. 2, the rack 110 holding the sample container 100 is transported to the sample aspirating position 300 by the rack transporter 42 of the sample transporter 4. Then, the arm 5a (pipette 5b), sample container 100 on the rack 110, and the pipette path 48a of the pipette washing unit 48 can be accurately positioned at the sample aspirating position 300 (refer to FIG. 14) based on the output signals of the θ encoder 72b and the output signals of the encoder 45 of the sample transporter 4. Note that while the sample container 100 to be aspirated is being transported to the sample aspirating position 300, the cap sensor 46 (refer to FIG. 3) detects whether a cap 101 is present or absent from the sample container 100.

Figure 12A:
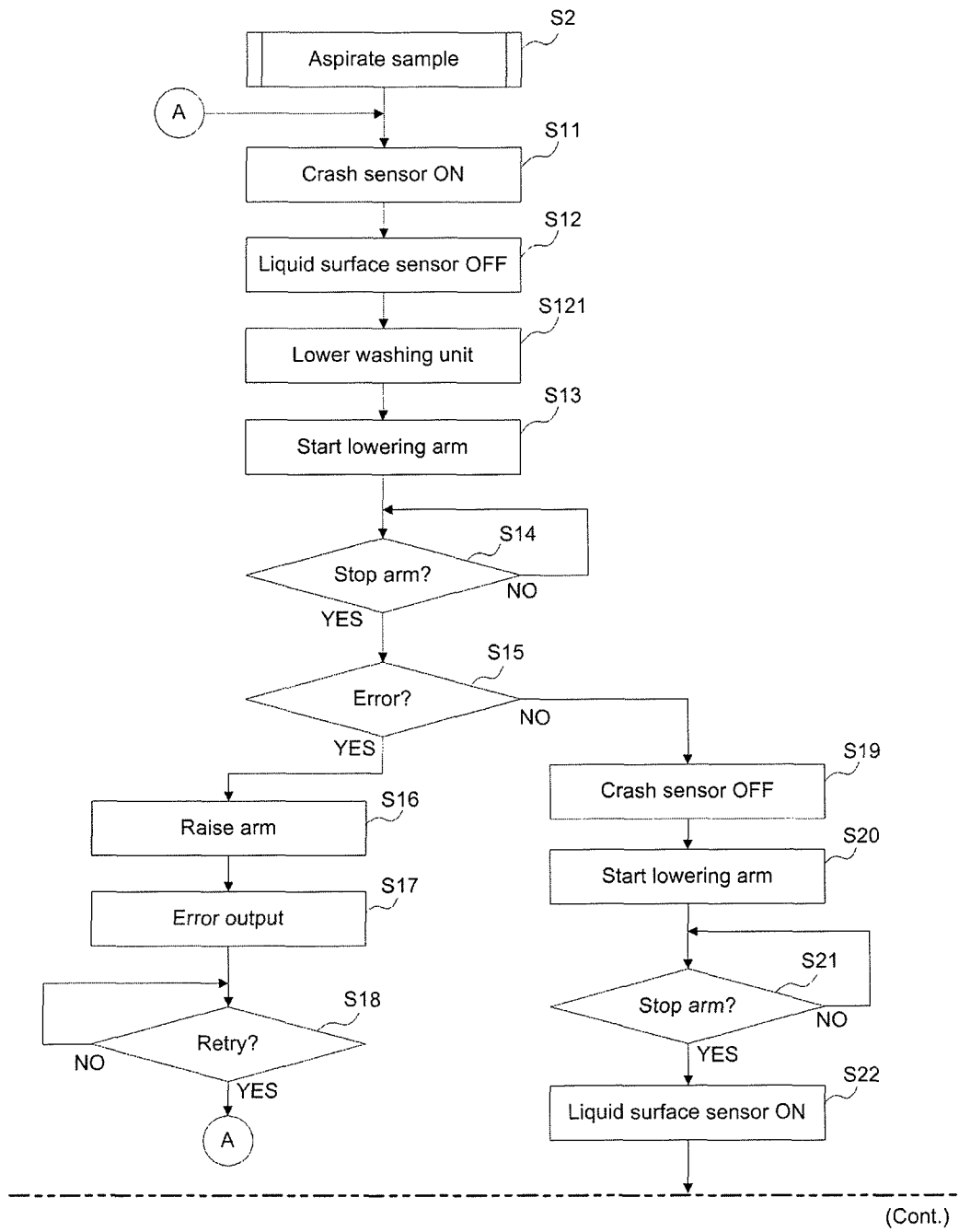
FIGS. 12A and 12B is a flow chart illustrating the sample aspiration process of the first sample dispensing arm of the embodiment of the present invention of FIG. 11.
Figure 13A:
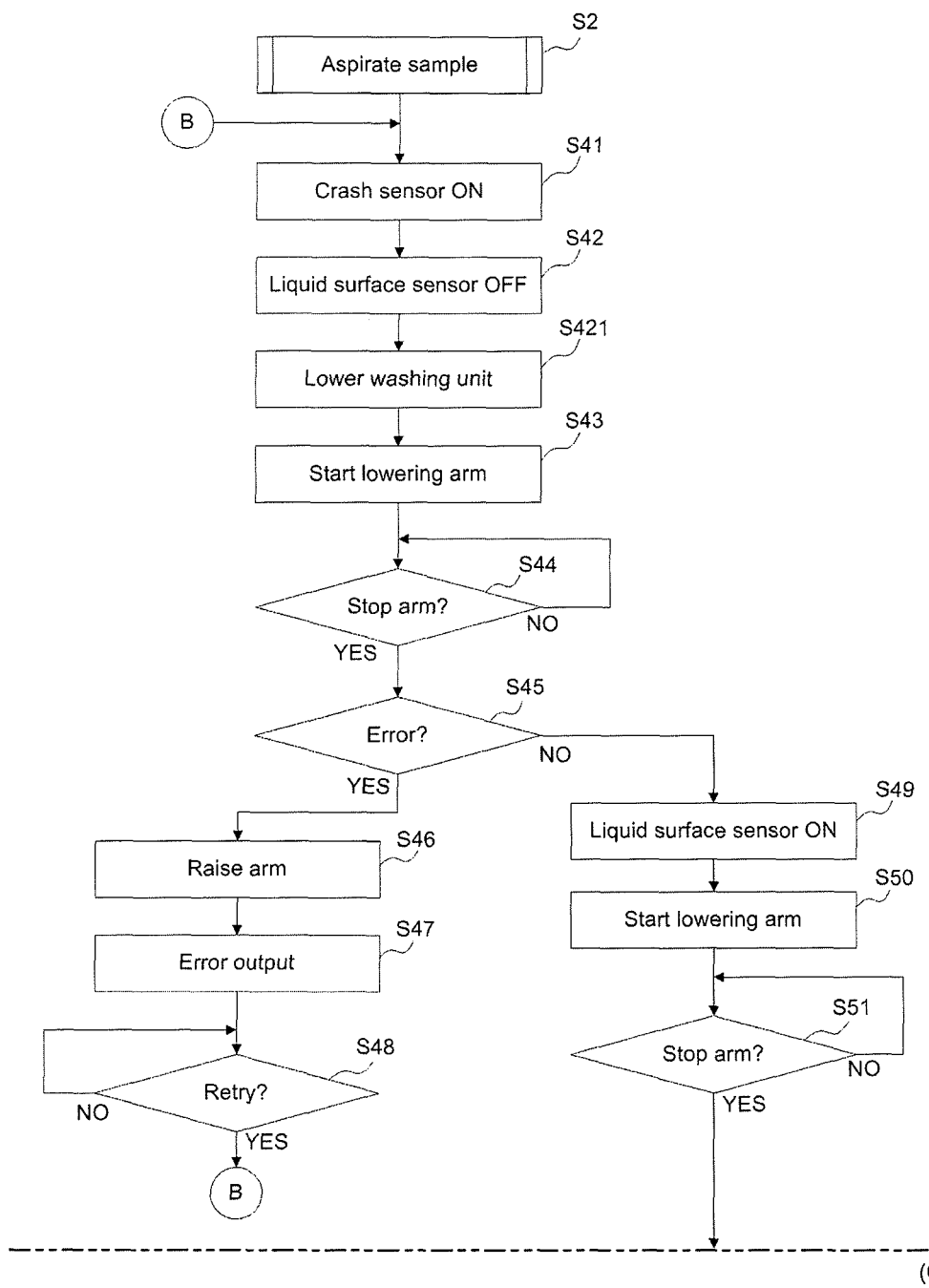
FIGS. 13A and 13B is a flow chart illustrating the sample aspiration process of the first sample dispensing arm of the embodiment of the present invention of FIG. 11.
Figure 13B:
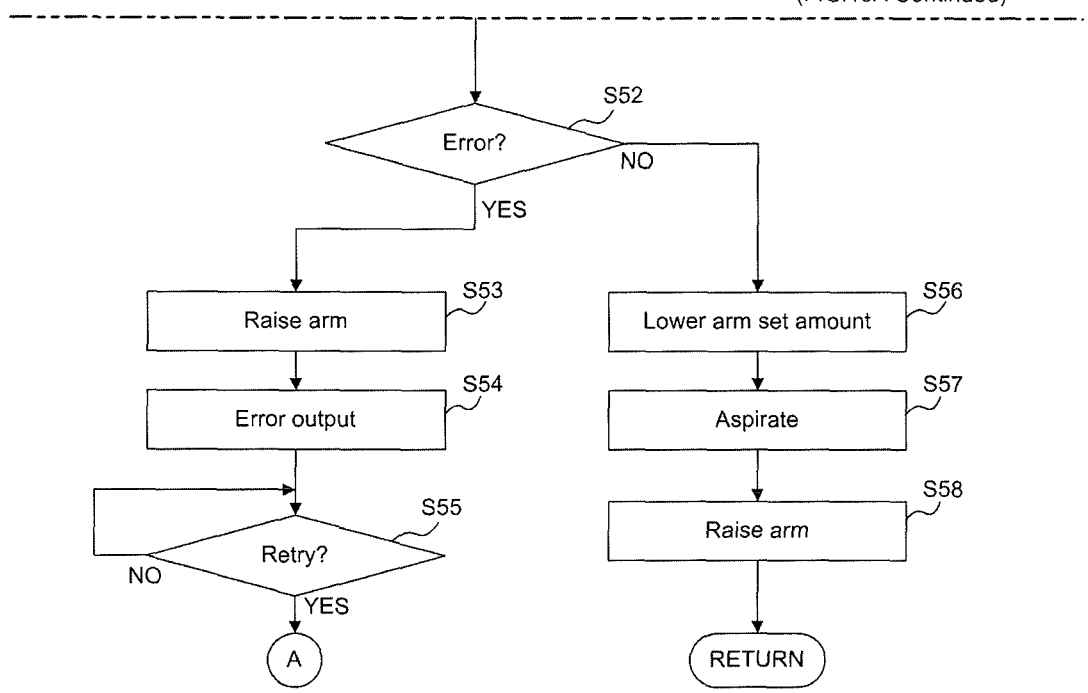

When the movements of the first sample dispensing arm 5 and rack 110 are completed, the sample is aspirated in step S2. The operation during sample aspiration is different depending on whether a cap 101 is present or absent from the sample container 100. The main controller 20 obtains the detection result (presence/absence of a cap 101) from the cal sensor 46 while the sample container 100 is being transported, and performs the sample aspiration process according to the presence or absence of the cap 101 of the sample container 100. Accordingly, the sample aspiration process of step S2 is performed when a cap is present as shown in FIG. 12A and when a cap is absent as shown in FIG. 13A. Note that the respective sample aspirating processes will be described later.

When the sample aspiration process is completed in step S2, the routine advances to step S3 and the arm 5a is rotated by the θ drive motor 72a (refer to FIG. 5) until the pipette 5b is positioned over the dispensing position. That is, the pipette 5b is disposed at a predetermined position above a cuvette placed in the cuvette unit 7 or above a cuvette placed in the cuvette transporter 12, as shown in FIG. 2.

In step S4, the arm 5a (pipette 5b) is lowered by the Z drive motor 73a (refer to FIG. 5) to the dispensing position above the cuvette, and sample is dispensed to the cuvette by discharging the sample from the pipette 5b by driving the syringe motor 74c (refer to FIG. 5).

Accordingly, the sample dispensing operation by the first sample dispensing arm 5 is completed as described above. After completion of the sample dispensing operation, the cuvette containing the dispensed sample is moved to the reactor 13 by the cuvette transporter 12 and the cuvette unit 16, on, and reagents are dispensed to the cuvette via the reagent dispensing arms 9, 10, and 11. After the sample and reagent have been reacted in the reactor 13, the cuvette is moved from the reactor 13 to the detecting unit 14 by the catcher unit 18, and the measurement sample within the cuvette is subjected to optical measurements.

The sample aspiration process for a capped container 100 in step S2 of FIG. 11 is described below with reference to FIGS. 1, 4, 5, 8, 10 through 12, and FIGS. 14 and 15.

As shown in FIG. 12A, the crash sensor 55 is turned ON in step S11 when the container 100 has a cap 101. That is, the switching circuit 83 allows the detection signal (limit signal) of the crash sensor 55 to be output the Z motor control circuit 82 (crash sensor ON), as shown in FIG. 4, based on the switch ON signal output from the Z motor control circuit 82. The liquid surface sensor 56 is turned OFF in step S12. That is, the switching circuit 83 blocks the detection signal (limit signal) of the liquid surface sensor 56 (liquid surface sensor OFF) based on the switch OFF signal output from the Z motor control circuit 82.

Figure 14:
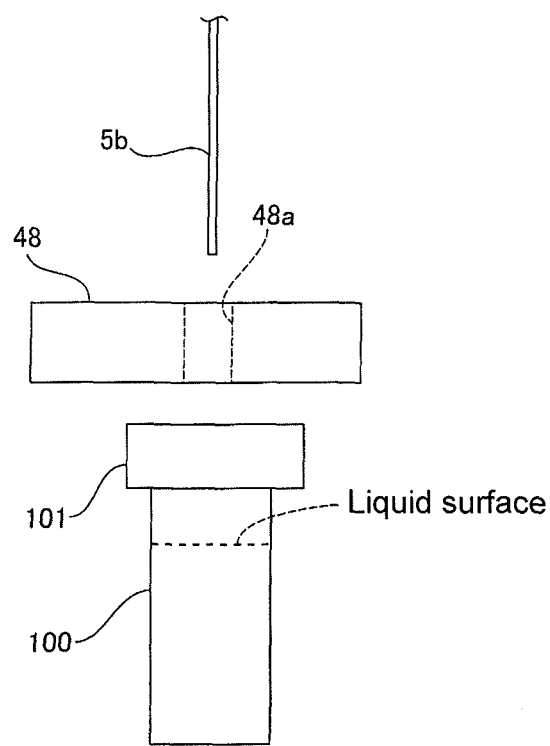
FIG. 14 is a schematic view showing the vertical disposition of the pipette, pipette washing unit, and sample container at the sample aspirating position (before the pipette washing unit is lowered)
Figure 15:
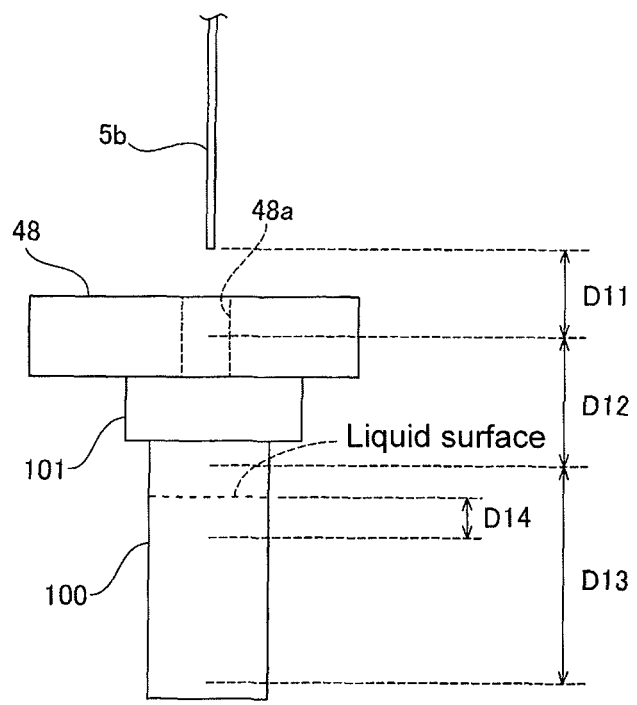
FIG. 15 is a schematic view illustrating the sample aspirating process (capped container) at the sample aspirating position.

In step S121, the washing unit 48 is lowered a predetermined amount from the position shown in FIG. 14 by the actuation of a motor not shown in the drawing, based on a control instruction of the controller 3a. Therefore, the cap 101 of the sample container 100 is pressed downward as shown in FIG. 15.

In step S13, the Z drive motor 73a is actuated and starts lowering the arm 5a. As shown in FIG. 15, a drive instruction is output from the main controller 20 (CPU 21) to lower the tip of the pipette 5b a predetermined amount (distance D11) to enter the path of the pipette washing unit 48. When the pipette 5b is not accurately positioned relative to the cap 101 of the sample container 100, the pipette collides with the margin of the path and lowering of the pipette 5b is stopped because the pipette 5b cannot enter the pipette path 48a.

Thus, the accurate positioning of the pipette 5b relative to the cap 101 can be confirmed by turning ON the crash sensor 55 until the pipette 5b enters the pipette path 48a. In the present embodiment, the pipette 5b must be accurately positioned relative to the cap 101 in order to turn OFF the crash sensor 55 at a position above the cap 101 and lower the pipette 5b to penetrate the cap 101 with the crash sensor 55 turned OFF, as will be described later. In the present embodiment, the crash sensor can be safely turned OFF by confirming that the pipette 5b is accurately positioned above the cap 1201 before the pipette 5b penetrates the cap 101.

Note that in step S12 the tip of the pipette 5b passes through the pipette path 48a of the pipette washing unit 48 without detecting the liquid surface when there is residual liquid from washing the pipette 5b in the pipette washing unit 48 by turning OFF the liquid surface sensor 56.

In step S14, the main controller 20 determines whether the arm 5a is stopped. When the arm 5a has been lowered the predetermined amount (distance D11) based on the drive instructions, the lowering of the arm 5a is stopped and a drive stop report is transmitted from the sub controller 80 to the main controller 20. When the tip of the pipette 5b comes into contact with an object while the crash sensor 55 is turned OFF, the pipette 5b (oscillating member 64) is raised by the support member 52 as shown in FIG. 10. In this case, a limit signal is output from the crash sensor 55 when the crash sensor 55 detects the detection piece 65a. As shown in FIG. 4, the lowering of the arm 5a is stopped and an error report is output from the sub controller 80 to the main controller 20 when the limit signal is received by the Z motor control circuit 82 through the switching circuit 83. When the halting of the arm 5a has been confirmed based on the drive stop report or error report, the routine advances to step S15.

As shown in FIG. 12A the main controller 20 determines whether an error has occurred in step S15. When the error report from the sub controller 80 is received, the routine advances to step S16 and the arm 5a is raised. That is, a drive instruction is output to raise the arm 5a until a limit signal of the upper limit sensor 87 (refer to FIG. 4) is received from the main controller 20 (CPU 21). When the Z drive motor 73a is actuated and the elevation of the arm 5a is completed, the routine advances to step S17 and a message indicating a collision of the pipette 5b, that is, "Pipette Crash," is displayed (error output) on the display 3b (refer to FIG. 1) of the control device 3. Thereafter, in step S18, the main controller 20 determines whether a retry instruction has been received based on the user operation of the control device 3. After the object involved in the collision has been removed and a retry instruction has been transmitted, the routine returns to step S11 and the sample aspiration operation is restarted.

On the other hand, when a drive stop report has been transmitted, the main controller 20 determines there is no error and the routine advances to step S19. In step S19 the crash sensor 55 is turned OFF. That is, as shown n FIG. 4, the switching circuit 83 blocks the detection signal (limit signal) of the crash sensor 55 (crash sensor OFF) based on the switch OFF signal output from the Z motor control circuit 82. Hence, the arm 5a lowering operation is performed but not on the basis of the detection result of either the crash sensor 55 or the liquid surface sensor 56.

In step S20, the Z drive motor 73a is actuated and starts lowering the arm 5a. As shown in FIG. 15, the main controller 20 (CPU 21) outputs a drive instruction to lower the tip of the pipette 5b a predetermined amount (distance D12) to penetrate the cap 101 of the sample container 100. Note that in steps S12 and S19 the lowering of the arm 5a is stopped by the output of a detection signal (limit signal) when the tip of the pipette 5b comes into contact with the cap 101 of the sample container 100 by turning OFF both the crash sensor 55 and the liquid surface sensor 56. In FIG. 14, when the sample container 100 and the pipette 5b within the pipette path 48a of the pipette washing unit 48 are confirmed to be accurately positioned vertically at the sample aspirating position 300 (refer to FIG. 2 and FIG. 15), there is no concern that the tip of the pipette 5b will come into contact with any part other than the cap 101 of the sample container 100.

During contact with the cap 101 of the sample container 100, the coil spring 68 is elastically deformed by the counter action of the cap 101 and the pipette 5b is raised relative to the support member 52 by the distance D1, as shown in FIGS. 8 and 10. Hence, the shock during contact of the cap 101 and the tip of the pipette 5b is absorbed. At this time the upward movement of the pipette 5b is stopped by the contact between the top end surface 67b of the engaging member 67 and the bottom surface of the support member 52. As shown in FIG. 10, when the arm 5a is further lowered after the tip of the pipette 5b comes into contact with the cap 101, the drive force of the Z drive motor 73a is fully transmitted to the cap 101 and is not absorbed by the coil spring 68 since this time the pipette 5b is lowered so that the bottom surface of the support member 52 presses against the top end surface 67b of the engaging member 67. Thus, the tip of the pipette 5b penetrates the cap 101. The lowering of the pipette 5b is stopped when the arm 5a has been lowered a predetermined amount (distance D12; refer to FIG. 15) after the tip of the pipette 5b penetrates the cap 101.

In step S21, the main controller 20 determines whether the arm 5a is stopped. When the arm 5a has been lowered the predetermined amount (distance D11) based on the drive instructions, the lowering of the arm 5a is stopped and a drive stop report is transmitted from the sub controller 80 to the main controller 20. When the main controller 20 receives the drive stop report, the routine advances to step S22.

In step S22 the liquid surface sensor 56 is turned ON. That is, the switching circuit 83 allows the detection signal (limit signal) of the liquid surface sensor 56 to be output the Z motor control circuit 82 (liquid surface sensor ON), as shown in FIG. 4, based on the switch ON signal output from the Z motor control circuit 82.

Figure 12B:
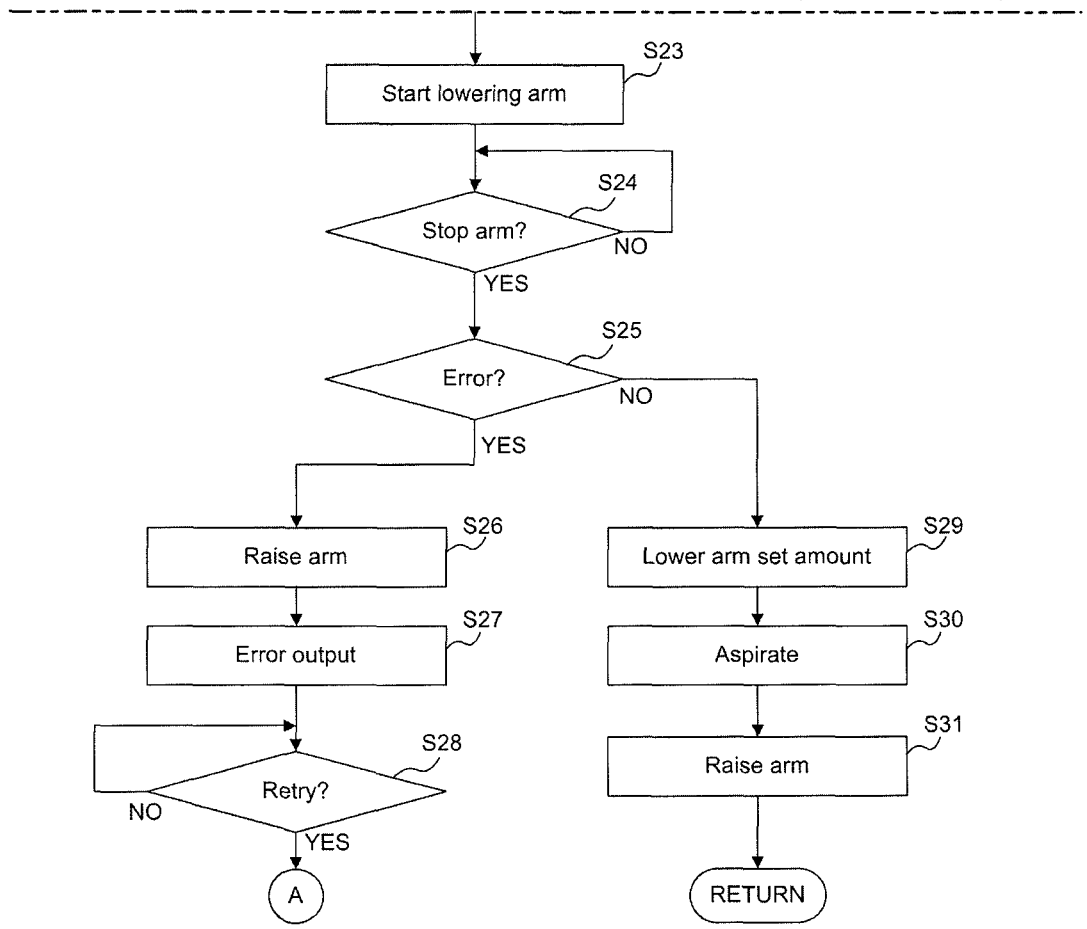

In step S23 of FIG. 12B, the Z drive motor 73a is actuated and starts lowering the arm 5a. In this case, a drive instruction is output from the main controller 20 (CPU 21) to lower the pipette 5b a predetermined amount (distance D13; refer to FIG. 15) until the tip of the pipette 5b is in the vicinity of the bottom of the sample container 100 (lower limit position).

In step S24, the main controller 20 determines whether the arm 5a is stopped. When the tip of the pipette 5b reaches the sample (liquid surface), a detection signal (limit signal) is output from the liquid surface sensor 56 and the lowering of the arm 5a is stopped and a drive stop report is transmitted to the main controller 20. On the other hand, when the liquid surface is not detected after lowering the arm 5a the predetermined amount (distance D13; refer to FIG. 15), the lowering of the arm 5a is stopped and an error report is transmitted to the main controller 20. When the halting of the arm 5a has been confirmed based on the drive stop report or error report, the routine advances to step S25.

In step S25 the main controller 20 determines whether an error has occurred. When the main controller 20 determines that an error has occurred based on the error report, the routine advances to step S26. That is, when the pipette 5b is lowered the predetermined amount (distance D13; refer to FIG. 15) and reaches the lower limit position without the liquid surface being detected, there is no remaining sample within the sample container 100 to be aspirated. Therefore, the arm 5a is raised to the upper limit position in step S26 without aspirating the sample. When the arm 5a has been raised fully, the routine advances to step S27 and the message (error output) "No Sample" indicating there is no sample in the sample container 100 to be aspirated is displayed on the display 3b of the control device 3. Thereafter, in step S28, the main controller 20 determine whether a retry instruction has been received based on the user operation of the control device 3. When the retry instruction is received, the routine returns to step S11 and the sample aspiration operation is restarted.

On the other hand, when the arm 5a is stopped based on the detection signal (limit signal) of the liquid surface sensor 56 and a drive stop report is received by the main controller 20, an error is not determined in step S25 of FIG. 12B, and the routine advances to step S29. In step S29, a drive instruction is output from the main controller 20 (CPU 21) to lower the arm 5a a predetermined amount (distance D14; refer to FIG. 15) corresponding to the amount of sample to be aspirated. The Z drive motor 73a is actuated based on this drive instruction, and starts lowering the arm 5a.

In step S30, the sample is aspirated at the position of the predetermined amount (distance D14; FIG. 15) below the liquid surface corresponding to the amount of sample to be aspirated. That is, the syringe motor 74c is actuated and sample is aspirated by the pipette 5b. Thus, the first sample dispensing arm 5 aspirates a predetermined amount of the sample. Thereafter, the routine advances to step S31, and the arm 5a is raised to the upper limit position to end the sample aspiration operation. Then, the routine moves to the operation of step S3 and subsequent steps in FIG. 11.

The sample is thus aspirated from the sample container 100 which has a cap 101.

The sample aspiration process for an uncapped container 100 in step S2 of FIG. 11 is described below with reference to FIGS. 1, 4, 5, 10, 11, 13, 14, and 16.

As shown in FIG. 13A, the crash sensor 55 (refer to FIG. 4) is turned ON in step S41 when the container 100 is uncapped. In step S42, the liquid surface sensor 56 (refer to FIG. 4) is turned OFF.

In step S421, the washing unit 48 is lowered a predetermined amount by actuating a motor (not shown in the drawing). Note that the heights of the capped and uncapped sample containers 100 are different Therefore, although the cap 101 is pressed downward by lowering the washing unit 48 when the sample container is capped, the washing unit 48 is stopped at a position above the top end of the sample container 100 when the container is uncapped (refer to FIG. 16).

Figure 16:
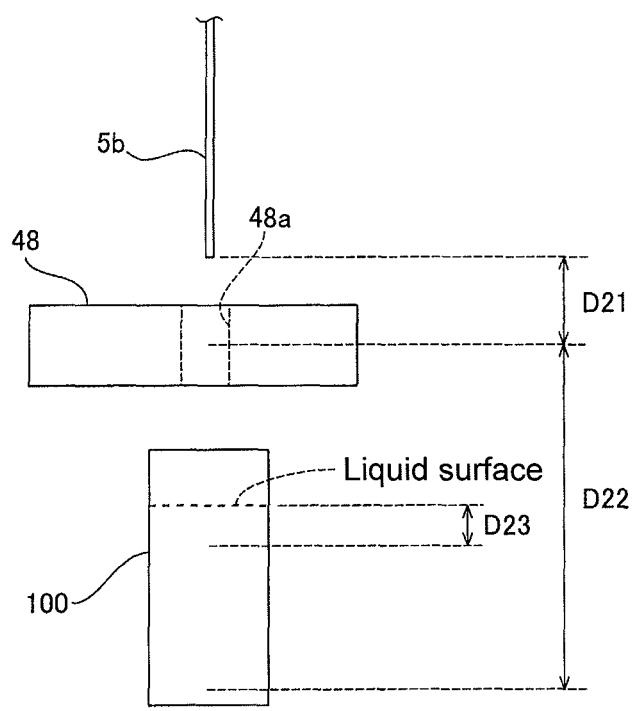
FIG. 16 is a schematic view illustrating the sample aspirating process (uncapped container) at the sample aspirating position.

In step S43, the Z drive motor 73a is actuated and starts lowering the arm 5a. In this case, a drive instruction is output from the main controller 20 (CPU 21) to lower the tip of the pipette 5b a predetermined amount (distance D21; FIG. 16) to insert the pipette tip in the path of the pipette washing unit 48.

In step S44, the main controller 20 determines whether the arm 5a is stopped. When the arm 5a has been lowered the predetermined amount (distance D21; FIG. 16), the lowering of the arm 5a is stopped and a drive stop report is transmitted to the main controller 20. When the tip of the pipette 5b comes into contact with an object (refer to FIG. 10), a limit signal is output from the crash sensor 55. Thus, the lowering of the arm 5a is stopped and an error report is output to the main controller 20. When the halting of the arm 5a has been confirmed based on the drive stop report or error report, the routine advances to step S45.

In step S45 the main controller 20 determines whether an error has occurred. When the error report from the sub controller 80 is received, the routine advances to step S46 and the arm 5a is raised to the upper limit position. In step S47, a message indicating a collision of the pipette 5b is displayed on the display 3b of the control device 3 (refer to FIG. 1). Then, in step S48, the main controller 20 determines whether a retry instruction has been received based on user operation of the control device 3; when a retry instruction has been received, the routine returns to step S42 and the sample aspiration operation is restarted.

On the other hand, when a drive stop report has been transmitted, the main controller 20 determines there is no error in step S45 and the routine advances to step S49. Since the pipette 5b need not penetrate the cap 101 when the sample container 100 is uncapped, the crash sensor 55 is normally turned ON, and operation controls are performed normally based on the detection result of the crash sensor 55. Since the sample container is uncapped and without a cap 101 (refer to FIG. 14), the pipette 5b passes through pipette washing unit 48 and the liquid surface detection operation is immediately performed. Hence, the liquid surface sensor 56 is turned ON in step S49.

In step S50, the lowering of the arm 5a begins. In this case, a drive instruction is output from the main controller 20 (CPU 21) to lower the pipette 5b a predetermined amount (distance D22; refer to FIG. 16) until the tip of the pipette 5b is in the vicinity of the bottom of the sample container 100 (lower limit position).

In step S51, the main controller 20 determines whether the arm 5a is stopped. When the tip of the pipette 5b reaches the sample (liquid surface), a detection signal (limit signal) is output from the liquid surface sensor 56 and the lowering of the arm 5a is stopped and a drive stop report is transmitted to the main controller 20. On the other hand, when the liquid surface is not detected after lowering the arm 5a the predetermined amount (distance D22; refer to FIG. 16), the lowering of the arm 5a is stopped and an error report is transmitted to the main controller 20. When the halting of the arm 5a has been confirmed based on the drive stop report or error report, the routine advances to step S52.

In step S52 the main controller 20 determines whether an error has occurred. When the pipette 5b is lowered the predetermined amount (distance D22) and reaches the lower limit position without detection of the liquid surface, the main controller 20 determines that an error has occurred based on the error report, and the routine continues to step S53. In step S53 the arm 5a is raised to the upper limit position and the routine moves to step S54. In step S54, a message "No Sample" message is generated indicating there is no sample in the sample container 100 to be aspirated, and the message is displayed on the display 3b of the control device 3 (refer to FIG. 1). Thereafter, in step S55, the main controller 20 determines whether a retry instruction has been received based on the user operation of the control device 3. When the retry instruction is received, the routine returns to step S41 and the sample aspiration operation is restarted.

On the other hand, when the arm 5a is stopped based on the detection signal (limit signal) of the liquid surface sensor 56, no error is determined in step S52 and the routine continues to step S56. In step S56, the Z drive motor 73a is actuated to lower the arm 5a a predetermined amount (distance D23; FIG. 16) corresponding to the amount of sample to be aspirated, and the lowering of the arm 5a begins.

In step S57, the sample is aspirated at the position of the predetermined amount (distance D23; FIG. 16) below the liquid surface corresponding to the amount of sample to be aspirated. Thereafter, the routine advances to step S58, and the arm 5a is raised to the upper limit position to end the sample aspiration operation. Then, the routine moves to the operation of step S3 and subsequent steps in FIG. 11.

The sample is thus aspirated from the sample uncapped container 100 which does not have a cap 101.

The embodiment described above is provided with a crash sensor 55 which detects a collision of the pipette 5b with an obstacle, and a sub controller 80 which controls the Z drive motor 73a so as to lower the pipette 5b to a height (D11; FIG. 15) above the cap 101 of the sample container 100, and thereafter to penetrate the cap 101 regardless whether the crash sensor 55 detects a collision of the pipette 5b after the pipette 5b has been lowered to a predetermined height (distance D11) above the cap 101 of the sample container 100 when aspirating a sample from a sample container 100 on which a cap 101 has been detected by the cal sensor 46. According to this configuration, when aspirating a sample from a sample container 100 with a cap 101, the lowering of the pipette 5b is stopped to prevent damage to the pipette 5b when the pipette 5b has collided with an obstacle while the pipette 5b was being lowered to a predetermined height (distance D11) above the cap 101. When the pipette 5b is lowered from the predetermined height, the pipette collides with the cap 101 and is further lowered so as to penetrate the cap 101 since the pipette 5b is lowered regardless of whether a pipette 5b collision is detected by the crash sensor 55. Hence, this simple structure rather than a complex structure avoids an external force activating the crash sensor 55. This simple structure also prevents damage to the pipette 5b and allows suitable lowering and aspiration operations to be performed by the pipette 5b.

In this embodiment, when aspirating a sample from the uncapped sample container 100 without a cap 101 based on the detection of the cap sensor 46, the sub controller 80 (Z motor control circuit 82) controls the Z drive motor 73a to stop lowering the pipette 5b when the crash sensor 55 has detected a collision of the pipette 5b. According to this configuration, sample can be aspirated from the uncapped sample container 100 (refer to FIG. 16) while preventing damage to the pipette 5b caused by a collision of the pipette 5b and an obstacle.

In the present embodiment, when the pipette 5b is lowered regardless of whether the crash sensor 55 has detected a collision of the pipette 5b, the output of the detection signal from the crash sensor 55 to the Z motor control circuit 82 is blocked by the switching circuit 83. According to this configuration, the pipette 5b can be easily lowered regardless of whether a pipette 5b collision is detected by the crash sensor 55 via simple signal processing to block the detection signal.

In the present embodiment described above, when the pipette 5b is lowered regardless of the crash sensor 55 detecting a collision of the pipette 5b, the sub controller 80 (Z motor control circuit 82) switches the switching circuit 83 so as to prevent the output of the detection signal to the Z motor control circuit 82 in response to instruction from the main controller 20. According to this configuration, the detection signal (limit signal) can be blocked simply by switching the switching circuit 83. Hence, a configuration is realized for lowering the pipette 5b regardless of the detection of a pipette 5b collision by the crash sensor 55 at the electronic circuit level.

In the embodiment described above, the Z motor control circuit 82 stops the output of the pulse signal when the detection signal (limit signal) is received from the crash sensor 55. According to this configuration, the Z motor control circuit 82 quickly stops the lowering of the pipette 5b when the pipette 5b collides with an obstacle other than the cap 101 regardless of the determination by software (software executed by the main controller 20) since the Z motor control circuit 82 stops the output of the pulse signal when a detection signal is received from the crash sensor 55. Therefore, damage to the pipette 5b is reliably prevented when the pipette 5b collides with an obstacle other than the cap 101.

In the embodiment described above, the pipette 5b is lowered while the crash sensor 55 is turned OFF until the tip of the pipette 5b reaches a predetermined height (D11; FIG. 15) advancing in the pipette washing path 48a (steps S13 and S14 in FIG. 12A). According to this configuration, when the pipette 5b is not accurately positioned relative to the cap 101 of the sample container 100 for whatever reason, the pipette 5b collides with the margin of the path without advancing in the pipette path 48a of the pipette washing unit 48, and the lowering of the pipette 5b is stopped based on the detection result of the crash sensor 55. Hence, damage to the pipette 5b as it is being lowered is prevented but not based on the detection result of the crash sensor 55 while the pipette 5b is not accurately positioned.

In the embodiment described above, when aspirating sample from a sample container 100 with a cap 101 detected by the cap sensor 46, the controller 3a lowers the pipette washing unit 48 so that the pipette washing unit 48 presses downward against the cap 101 of the sample container 100. According to this configuration, the distance is minimized between the pipette washing unit 48 and the cap 101 of the sample container 100. Thus, it is possible to reduce the crash of the pipette 5b with an obstacle other than the cap 101 occurring for whatever reason when the pipette 5b is lowered but not based on the detection result of the crash sensor 55. Furthermore, wobbling of the sample container 100 can be reduced when penetrating the cap 101 by pressing the cap 101 of the container 100 downward, and lifting of the sample container 100 can be reduced when the pipette 5b that has penetrated the cap 101 is thereafter extracted therefrom.

In the embodiment described above, when the liquid surface sensor 56 detects the pipette 5b has reached the liquid surface, the main controller 20 controls the Z drive motor 73a so as to lower the pipette 5b a predetermined amount (distance D14 or D23; refer to FIGS. 15 and 16), and controls the syringe pump unit 74 so as to aspirate the sample after lowering the pipette 5b a predetermined amount (distance D14 or D23). According to this configuration, the sample is aspirated when the pipette 5b is lowered a predetermined amount (distance D14 or D23) from the liquid surface. Thus, the sample can be reliably aspirated while preventing before it occurs the aspiration of air that may occur when starting the aspiration at a shallow position below the liquid surface by aspirating the sample when the pipette 5b has been lowered a predetermined amount (distance D14 or D23) below the liquid surface.

In the embodiment described above, the sub controller 80 (Z motor control circuit 82) controls the Z drive motor 73a so as to lower the pipette 5b regardless of the detection result of the liquid surface sensor 56 until the tip of the pipette 5b passes through the pipette washing unit 48. According to this configuration, it is possible to prevent detection errors caused by the liquid surface sensor 56 detecting the residual washing liquid as the pipette 5b transits the path through the pipette washing unit 48 even when washing liquid remains in the pipette washing unit 48.

In the embodiment described above, the crash sensor 55 detects the collision of the pipette 5b when the pipette 5b is moved upward relative to the support member 52. According to this configuration, the pipette 5b is not moved upward relative to the support member 52 insofar as there is no physical collision with an obstacle, and a collision can be reliably detected when the pipette 5b does collide with an obstacle.

In the embodiment described above, when the predetermined positional relationship of the crash sensor 55 and the detected member 65 is lost due to the pipette 5b moving upward relative to the support member 52 (that is, when the detection piece 65a of the detected member 65 blocks the crash sensor 55), the crash sensor 55 detects the collision of the pipette 5b. In this configuration, a collision of the pipette 5b can be detected by reliably detecting the upward movement of the pipette 5b via a simple structure.

In the embodiment described above, a coil spring 68 is provided to exert a downward force on the pipette 5b relative to the support member 52 when the pipette 5b is moved upward relative to the support member 52. According to this configuration, the pipette 5b is naturally returned to the pre-collision position by the coil spring 68 when the pipette 5b is removed from an obstacle even though the pipette 5b is moved upward relative to the support member 52 by the collision with the obstacle.

In the embodiment described above, the pipette 5b penetrates the cap 101 while the movement of the pipette 5b relative to the support member 52 is regulated by the engaging member 67. According to this configuration, sufficient drive force is transmitted from the Z drive motor 73 to the pipette 5b when the pipette 5b penetrates the cap 101 of the sample container 100 by suppression of the wobbling of the pipette 5*b* even when the pipette 5*b* is moved upward relative to the support member 52.

In the embodiment described above, a rack transporter 42 is provided which transports the rack 110 holding the sample container 100, and the cap sensor 46 detects the cap 101 of the sample container 100 based on whether light from a light emitter 46*a* is received by a light receiver 46*b*. According to this configuration, the cap 101 of the sample container 100 held in the rack 110 is detected while the rack 110 is being transported. Hence, the presence of a cap 101 on the sample container 100 can be quickly determined.

Note that in the embodiment of this disclosure are in all respects examples, and in no way intended to be limiting. The scope of the present invention is represented in the scope of the claims and not the description of the embodiments, and may be variously modified insofar as such modification is within the scope of the claims and equivalences in meaning.

For example, although the above embodiment is described by way of example in which the pipette 5*b* is mounted on the support member 52 using a retaining member 61, oscillating member 64, engaging member 67, and spacer 69 that rise integratedly with the pipette 5*b* relative to the support member 52, the present invention is not limited to this configuration. In the present invention, different structures than the retaining member 61, oscillating member 64, engaging member 67 and spacer 69 may be used insofar as such structures support the pipette so as to be liftable relative to the support member.

Although the above embodiment is described by way of example providing a coil spring 68 as an example of the elastic member of the present invention, the present invention is not limited to this configuration. In the present invention, an elastic member other than a coil spring, such as a rubber elastic member, also may be used.

Although the above embodiment is described in terms of raising and lowering the support member 52 (arm 5*a*) by a step motor, the present invention is not limited to this configuration. For example, the support member may be raised and lowered using a servo motor or the like rather than a step motor.

Although the above embodiment provides a detected member 65 on the oscillating member 64, and detects the raising of the pipette 5*b* by the optical crash sensor 55 detecting the detection piece 65*a* of the detected member 65, the present invention is not limited to this configuration. For example, in the present invention a mechanical switch may be provided on the oscillating member to detect the raising of the pipette without providing the detected member.

Although the above embodiment is described in terms of the sub controller 80 stopping the Z drive motor 73*a* based on the detection signal (limit signal) of the crash sensor 55, the present invention is not limited to this configuration. In the present invention, the raising of the pipette (support member) slightly when the tip of the pipette abuts an object can be controlled by driving the Z drive motor in the reverse direction based on the detection signal (limit signal) of the crash sensor.

Although the above embodiment is described in terms of the controlling the drive of the Z drive motor 73*a* to lower the pipette 5*b* regardless of whether the crash sensor 55 detects a collision of the pipette 5*b* by blocking the output of the detection signal (limit signal) of the crash sensor 55 using the switching circuit 83 during the penetration of the cap 101 of the sample container 100, the present invention is not limited to this configuration. In the present invention, the drive of the Z drive motor may be controlled to lower the pipette 5*b* regardless of whether the crash sensor detects a pipette collision by turning OFF the crash sensor itself (stopping the power supply to the crash sensor).

Although the above embodiment is described in terms of the controlling the drive of the Z drive motor 73*a* to lower the pipette 5*b* regardless of whether the liquid surface sensor 56 detects that the pipette 5*b* has reached the liquid surface by blocking the output of the detection signal (limit signal) of the liquid surface sensor 56 using the switching circuit 83 during the penetration of the cap 101 of the sample container 100, the present invention is not limited to this configuration. In the present invention, the drive of the Z drive motor may be controlled to lower the pipette 5*b* regardless of whether the liquid surface sensor detects the pipette reaching the liquid surface by turning OFF the liquid surface sensor itself (stopping the power supply to the liquid surface sensor).

Although the above embodiment is described in terms of providing a main controller in the measuring device and providing a sub controller in the first sample dispensing arm, and controlling the drive of each part (Z drive motor, θ drive motor and the like) of the first sample dispensing arm via the sub controller based on the drive instruction from the main controller, the present invention is not limited to this configuration. In the present invention, the main controller may directly control the drive of each part of the first sample dispensing arm.

The invention claimed is:

1. A sample aspirating apparatus capable of aspirating a sample from both a capped container with a cap and an uncapped container, the sample aspirating apparatus comprising:
  a pipette which aspirates a sample, wherein the pipette is able to penetrate a cap of a capped container;
  a cap sensor which detects whether a cap is present or absent;
  a driving section which moves the pipette upward and downward;
  a crash sensor which detects a crash of the pipette with an obstacle; and
  a controller which controls the driving section to move the pipette, and stop the pipette when the crash sensor detects a crash by the pipette, wherein
  when aspirating a sample in a container with a cap which has been detected by the cap sensor, the controller controls the driving section to move the pipette downward regardless of the detection by the crash sensor and thereby cause the pipette to penetrate the cap.

2. The sample aspirating apparatus of claim 1, wherein when aspirating a sample from a container with a cap which has been detected by the cap sensor, the controller controllably moves the pipette based on the detection by the crash sensor until the tip of the pipette reaches a predetermined position above the cap, then moves the pipette downward from the predetermined position regardless of the detection by the crash sensor.

3. The sample aspirating apparatus of claim 1, wherein when aspirating a sample from a container and the cap sensor has not detected a cap, the controller controls the driving section controllably moves the pipette based on the detection by the crash sensor.

4. The sample aspirating apparatus of claim 1, wherein the crash sensor outputs a detection signal to the controller when the pipette crashes with an obstacle; and
  a sub controller blocks the detection signal sent from the crash sensor to the controller when moving the pipette regardless of the detection by the crash sensor.

5. The sample aspirating apparatus of claim 4, wherein the sub controller comprises a switching circuit which receives the detection signal from the crash sensor, and limits the output of the received detection signal to the controller.

6. The sample aspirating apparatus of claim 4, wherein
the controller comprises a drive control circuit which continuously outputs to the driving section a number of pulse signals in accordance with the amount of lowering of the pipette;
the driving section lowers the pipette according to the pulse signals received from the drive control circuit; and
the drive control circuit stops the output of the pulse signal when a detection signal is not received from the crash sensor.

7. The sample aspirating apparatus of claim 1, wherein
the controller controls the crash sensor not to output a detection signal when lowering the pipette regardless of the detection by the crash sensor.

8. The sample aspirating apparatus of claim 1, wherein
the controller controls the crash sensor not to detect a crash of the pipette when lowering the pipette regardless of the detection of the crash sensor.

9. The sample aspirating apparatus of claim 8, wherein
the crash sensor is configured to detect a crash of the pipette when electrical power is supplied; and
the controller controllably stops the supply of electrical power to the crash sensor when the pipette is lowered regardless of the detection of the crash sensor.

10. The sample aspirating apparatus of claim 2, further comprising a through path member which forms a path that is passable by the pipette and is disposed above the container to be aspirated; and
the predetermined position is the position at which the tip of the pipette locates in the path of the through path member.

11. The sample aspirating apparatus of claim 10, wherein
the through path member is vertically movable; and
the controller lowers the through path member so that the through path member presses downward on the cap of the sample container when the sample is aspirated from a capped container detected by the cap sensor.

12. The sample aspirating apparatus of claim 10, further comprising:
a liquid surface sensor which detects when the tip of the pipette reaches the surface of the sample in the container; and
a pump which applies a pressure to aspirate the sample,
wherein the controller controls the driving, section so as to lower the pipette when the liquid surface sensor detects that the tip of the pipette reaches the surface of the sample, and then controls the aspirating section so as to drive the pump and aspirate the sample.

13. The sample aspirating apparatus of claim 12, further comprising a washing section which washes the pipette by supplying a washing liquid to the pipette inserted in the path of the through path member, wherein
the controller controls the driving section so as to lower the pipette regardless of the detection result of the liquid surface sensor until the tip of the pipette passes through the through path member.

14. The sample aspirating apparatus of claim 1, further comprising a support member which movably supports the pipette upwardly relative to the support member;
the driving section is configured to move the pipette by moving the support member; and
the crash sensor detects a crash of the pipette when the pipette moves upwardly relative to the support member.

15. The sample aspirating apparatus of claim 14, wherein the crash sensor comprises
a sensing part provided on the support member; and
a sensed member provided on the pipette in a predetermined positional relationship with the sensing part;
wherein a crash of the pipette is detected when the predetermined positional relationship of the sensing part and the sensed member is not obtained due to the upward movement of the pipette relative to the support member.

16. The sample aspirating apparatus of claim 14, further comprising an elastic member which exerts a downward force on the pipette relative to the support member.

17. The sample aspirating apparatus of claim 14, further comprising a regulating member which regulates the upward movement of the pipette in excess of a predetermined amount relative to the support member, wherein
the pipette is configured so that the cap is penetrated while the upward movement relative to the support member is regulated by the regulating member.

18. The sample aspirating apparatus of claim 1, further comprising a transport path which transports a rack that holds the container, wherein
the cap sensor comprises an irradiating part which radiates light toward a predetermined height on the transport path, and a receiving part which receives the light from the irradiating part with the transport path interposed therebetween, such that the cap of the container is detected based on whether the light from the irradiating part is received by the receiving part.

19. The sample aspirating apparatus of claim 1, wherein
the controller causes the pipette to penetrate the cap of the container while the container is held in the rack.

20. A sample analyzer which measures and analyzes a measurement sample prepared by adding a reagent to the sample, the sample analyzer comprising:
the sample aspirating apparatus of claim 1;
a reagent dispensing section which adds reagent to a sample that has been aspirated by the sample aspirating apparatus; and
a detecting section which optically detects a component contained in the mixture of the sample and reagent.

\* \* \* \* \*